US012629371B2

(12) United States Patent
Werner et al.

(10) Patent No.: US 12,629,371 B2
(45) Date of Patent: May 19, 2026

(54) COMPOSITIONS AND METHODS FOR INHIBITING KINASES

(71) Applicant: Inhibikase Therapeutics, Inc., Atlanta, GA (US)

(72) Inventors: Milton H. Werner, Marietta, GA (US); Terence A. Kelly, Ridgefield, CT (US)

(73) Assignee: Inhibikase Therapeutics, Inc., Atlanta, GA (US)

( * ) Notice: Subject to any disclaimer, the term of this patent is extended or adjusted under 35 U.S.C. 154(b) by 277 days.

(21) Appl. No.: 16/342,730

(22) PCT Filed: Oct. 25, 2017

(86) PCT No.: PCT/US2017/058263
§ 371 (c)(1),
(2) Date: Apr. 17, 2019

(87) PCT Pub. No.: WO2018/081251
PCT Pub. Date: May 3, 2018

(65) Prior Publication Data
US 2020/0046699 A1      Feb. 13, 2020

Related U.S. Application Data

(60) Provisional application No. 62/412,600, filed on Oct. 25, 2016.

(51) Int. Cl.
*A61K 31/506*      (2006.01)
*A61P 25/28*      (2006.01)

(52) U.S. Cl.
CPC ............ *A61K 31/506* (2013.01); *A61P 25/28* (2018.01)

(58) Field of Classification Search
CPC .... A61K 31/506; A61K 45/06; A61K 31/541; A61K 31/5377; A61P 25/28; A61P 25/16
See application file for complete search history.

(56) References Cited

U.S. PATENT DOCUMENTS

| | | | |
|---|---|---|---|
| 9,828,370 | B2 | 11/2017 | Werner et al. |
| 10,118,923 | B2 | 11/2018 | Werner et al. |
| 10,316,031 | B2 | 6/2019 | Werner et al. |
| 10,344,027 | B2 | 7/2019 | Werner et al. |
| 10,906,896 | B2 | 2/2021 | Werner et al. |
| 11,407,747 | B2 | 8/2022 | Werner et al. |
| 11,725,005 | B2 | 8/2023 | Werner et al. |

(Continued)

FOREIGN PATENT DOCUMENTS

| | | |
|---|---|---|
| CN | 102406648 A | 4/2012 |
| JP | 2010/502726 A | 1/2010 |

(Continued)

OTHER PUBLICATIONS

Badaway, Salt Selection for Pharmaceutical Compounds, Salt Selection for Pharmaceutical Compounds, 2008, pp. 63-80. (Year: 2008).*

(Continued)

*Primary Examiner* — Renee Claytor
*Assistant Examiner* — Andrew P Lee
(74) *Attorney, Agent, or Firm* — Wolf, Greenfield & Sacks, P.C.

(57) ABSTRACT

The present invention provides methods for the prevention or treatment of Parkinson's Disease using Abelson-family tyrosine kinase inhibitors.

22 Claims, 7 Drawing Sheets

MPTP Mouse Model: Study Design

(56) References Cited

U.S. PATENT DOCUMENTS

| | | |
|---|---|---|
| 2010/0249122 A1 | 9/2010 | Kalman |
| 2020/0031819 A1 | 1/2020 | Werner et al. |
| 2020/0046699 A1 | 2/2020 | Werner et al. |
| 2021/0130343 A1 | 5/2021 | Werner et al. |
| 2023/0159514 A1 | 5/2023 | Werner et al. |
| 2025/0250266 A1 | 8/2025 | Werner et al. |

FOREIGN PATENT DOCUMENTS

| | | |
|---|---|---|
| WO | WO-2008/070350 A2 | 6/2008 |
| WO | WO-2008/079460 A2 | 7/2008 |
| WO | WO-2013/171642 A1 | 11/2013 |
| WO | WO-2014/055938 A1 | 4/2014 |
| WO | WO-2016/172528 A1 | 10/2016 |
| WO | WO-2018/081251 A1 | 5/2018 |

OTHER PUBLICATIONS

Saal, Pharmaceutical salts: A summary on doses of salt formers from the Orange Book, European Journal of Pharmaceutical Sciences, 2013, 49, pp. 614-623. (Year: 2013).*

Bosseray, et al., "What's new in vaccines against herpes simplex infections?" Pathol Biol (Paris), 50(8): 483-492 (2002). (Abstract).

Brahmachari et al., "c-Abl and Parkinson's Disease: Mechanisms and Therapeutic Potential," J Parkinsons Dis, 7(4):589-601 (2017).

Douglas, Jr., "Introduction to Viral Diseases," Cecil Textbook of Medicine, 20(2): 1739-1747 (1996).

Goff, "Intracellular trafficking of retroviral genomes during the early phase of infection: viral exploitation of cellular pathways," J Gene Med, 3(6): 517-528 (2001). (Abstract).

Gura, "Systems for Identifying New Drugs are Often Faulty," Science, 278(5340): 1041-1042 (1997).

Imam et al., "Novel RegulationofParkin Function Through C-Abl-Mediated Tyrosine Phosphorylation: Implications For Parkinson's Disease," J Neurosci, 31(1):157-163 (2011).

International Search Report and Written Opinion for International Application No. PCT/US2017/058263 dated Feb. 26, 2018.

Johnson, et al., "Relationships between drug activity in NCI preclinical in vitro and in vivo models and early clinical trials," Br J Cancer, 84(10): 1424-1431 (2001).

Karuppagounder et al., "The c-Abl inhibitor, nilotinib, protects dopaminergic neurons in a preclinical animal model of Parkinson's disease," Sci Rep, 4:4874 (2014).

Lindholm et al., "c-Abl inhibitors enable insights into the pathophysiology and neuroprotection in Parkinson's disease," Front Aging Neurosci, 8:254 (2016).

Napier et al., "Low Doses of Imatinib Induce Myelopoiesis and Enhance Host Anti-microbial Immunity," Plos Pathog, 1-27 (Mar. 30, 2015).

Pearce, et al., "Failure modes in anticancer drug discovery and development," Cancer Drug Design and Discovery: 424-435 (2008).

Razonable, et al., "Herpesvirus infections in transplant recipients: current challenges in the clinical management of cytomegalovirus and Epstein-Barr virus infections," Herpes, 10(3): 60-65 (2003). (Abstract).

Simone, "Oncology: Introduction," Cecil Textbook of Medicine, 20(1): 1004-1010 (1996).

Bommarius et al., "Enteropathogenic Escherichia coli Tir is an SH2/3 ligand that recruits and activates tyrosine kinases required for pedestal formation," Molecular Microbiology, 63(6):1748-1768 (2007).

Burton et al., "Abl tyrosine kinases are required for infection by Shigella flexneri," The EMBO Journal, 22(20):5471-5479 (2003).

Coleman et al., "Abelson Kinase Inhibitors Are Potent Inhibitors of Severe Acute Respiratory Syndrome Coronavirus and Middle East Respiratory Syndrome Coronavirus Fusion," Journal of Virology, 90(19):8924-8933 (2016).

Dyall et al., "Repurposing of Clinically Developed Drugs for Treatment of Middle East Respiratory Syndrome Coronavirus Infection," Antimicrobial Agents and Chemotherapy, 58(8):4885-4893 (2014).

Elwell et al., "RNA Interference Screen Identifies Abl Kinase and PDGFR Signaling in Chlamydia trachomatis Entry," PLOS Pathogens, 4(3):e1000021 (2008).

Garcia et al., "Productive Replication of Ebola Virus is Regulated by the c-Abl1 Tyrosine Kinase," Science Translational Medicine, 4(123):123ra24 (2012).

Imam et al., "Neuroprotective Efficacy of a New Brain-Penetrating C-Abl Inhibitor in a Murine Parkinson's Disease Model," Plos One, 8(5): e65129 (2013).

Pagan et al., "Nilotinib Effects in Parkinson's Disease and Dementia with Lewy Bodies," Journal of Parkinson's Disease, 6: 503-517 (2016).

Pielage et al., "RNAi Screen Reveals an Abl Kinase-Dependent Host Cell Pathway Involved in Pseudomonas aeruginosa Internalization," PLOS Pathogens, 4(3):e1000031 (2008).

Reeves et al., "Disabling poxvirus pathogenesis by inhibition of Abl-family tyrosine kinases," Nature Medicine, 11(7):731-739 (2005).

Reeves et al., "Variola and Monkeypox Viruses Utilize Conserved Mechanisms of Virion Motility and Release That Depend on Abl and Src Family Tyrosine Kinases," Journal of Virology, 85(1):21-31 (2011).

Swimm et al., "Abl Family Tyrosine Kinases Regulate Sialylated Ganglioside Receptors for Polyomavirus," Journal of Virology, 84(9):4243-4251 (2010).

Swimm et al., "Cytosolic Extract Induces Tir Translocation and Pedestals in EPEC-Infected Red Blood Cells," PLOS Pathogens, 4(1):e4 (2008).

Swimm et al., "Enteropathogenic Escherichia coli Use Redundant Tyrosine Kinases to Form Actin Pedestals," Molecular Biology of the Cell, 15:3520-3529 (2004).

Uebelhoer et al., "High-throughput, luciferase-based reverse genetics systems for identifying inhibitors of Marburg and Ebola viruses," Antiviral Research, 106:86-94 (2014).

Wessler et al., "Abl Family of Tyrosine Kinases and Microbial Pathogenesis," International Review of Cell and Molecular Biology, 286:271-300 (2011).

Genital Herpes-CDC Fact Sheet, (http://www.cdc.gov/std/Herpes/STDFact-Herpes.htm), (2017).

Rytting, "Acute Leukemia," Merck Manual (Online Edition), 1-6 (2013).

Notice of Allowance for U.S. Appl. No. 17/141,825 issued Mar. 9, 2022.

Pagan et al., "Long-Term Safety and Clinical Effects of Nilotinib in Parkinson's Disease," Movement Disorders, 36(3): 740-749 (2021).

Simuni et al., "Efficacy of Nilotinib in Patients With Moderately Advanced Parkinson Disease," JAMA Neurology, 78(3): 312-320 (2021).

U.S. Appl. No. 15/136,497, Granted.
U.S. Appl. No. 15/805,693, Granted.
U.S. Appl. No. 16/169,677, Granted.
U.S. Appl. No. 16/169,683, Granted.
U.S. Appl. No. 16/452,828, Granted.
U.S. Appl. No. 17/141,825, Allowed.
Extended European Search Report for EP Application No. 17863419.2 mailed May 18, 2020.

* cited by examiner

MPTP Mouse Model:  Study Design

MPTP Mouse Model:  Body Weight on 14$^{th}$ Day

MPTP Mouse Model:  Pole Test

MPTP Mouse Model: Dopamine Levels

MPTP Mouse Model:  Metabolite Levels

Figure 5

MPTP Mouse Model:  Compound 809 Summary

COMPOSITIONS AND METHODS FOR INHIBITING KINASES

REFERENCE TO RELATED APPLICATIONS

This application is a § 371 national-stage application based on Patent Cooperation Treaty Application serial number PCT/US2017/058263, filed Oct. 25, 2017; which claims the benefit of priority to U.S. Provisional Application No. 62/412,600, filed Oct. 25, 2016, the contents of which are fully incorporated by reference herein in their entirety.

STATEMENT REGARDING FEDERALLY SPONSORED RESEARCH

The invention was made with Government support under Grant Number AI103982, awarded by the National Institutes of Health. The Government has certain rights in the invention.

BACKGROUND OF THE INVENTION

Parkinson's Disease

Parkinson's Disease is a progressive neurodegenerative disorder that affects approximately 1 million Americans and 7 to 10 million people worldwide. With people living longer, more people are developing this common, debilitating neurological disorder. Parkinson's disease is characterized by disorders of movement, which are caused by the progressive loss of dopamine-secreting neurons in the substantia nigra pars *compacta* (SNpc), along with autonomic nervous system dysfunction, anxiety, depression, sleep disorders and cognitive impairment that are due to the degeneration and dysfunction of other neuronal populations. To date there are no pharmaceutical therapies that impede or prevent the relentless neurodegeneration in PD. Although dopamine replacement alleviates symptomatic motor dysfunction, its effectiveness is reduced as the disease progresses, leading to unacceptable side effects, such as severe motor fluctuations and dyskinesias. Moreover, this palliative therapeutic approach does not address the underlying mechanisms of the disease. Current treatments for PD are symptomatic therapies with many limitations.

Abelson-family tyrosine kinases (ATKs), such as c-Abl1, c-Abl2, c-Kit (also known as SCF), PDGFRa, and PGDFRb, collectively referred to as c-Abl hereafter, have been implicated in certain neurological diseases, including Parkinson's disease. For example, parkin is a protein that plays a role in targeting other proteins for degradation, and is believed to have a protective function against Parkinson's disease. Aberrant activation of c-Abl can down-regulate parkin activity by phosphorylation. Thus ATK inhibitors may be useful as a therapy to prevent or treat Parkinson's disease. Similarly, c-Abl phosphorylation of alpha-synuclein both promotes aggregation of alpha-synuclein and is linked to the deleterious effects of alpha-synuclein on neurons in the brian.

The known ATK inhibitors, such as imatinib, were for the most part developed as cancer drugs, so measures of their risk: benefit ratio are skewed to higher risk when ATK inhibitors are applied to a life or death indication. A drug for Parkinson's Disease, on the other hand, would have to meet a more stringent standard of risk: benefit because the side effects would be experienced by patients chronically, often over a period of several decades. Moreover, ability to cross the blood brain barrier is important for a therapeutic to treat Parkinson's disease, but not relevant to treat most cancers that can currently be treated with ATK inhibitors.

The known ATK inhibitors imatinib and nilotinib appear effective in animal models of Parkinson's Disease (J. Neurosci. 31(1): 157-163, doi 10.1523/JNEUROSCI.1833-10.2011; Scientific Reports 4:4874, doi 10.1038/srep04874). However, the brain penetration of nilotinib is only 0.5% by mass when considering the amount of drug that crosses the blood brain barrier relative to the constant amount that exists in the blood. Another known ATK inhibitor, dasatinib, has a similar brain penetration. And imatinib's brain: blood ratio is just 5% by mass. All three drugs have serious side effects making them incompatible with their chronic use in Parkinson's patients.

Improved agents for treating Parkinson's Disease are needed.

SUMMARY OF THE INVENTION

In certain aspects, the invention provides methods of treating or preventing Parkinson's Disease comprising administering a therapeutically effective amount of an ATK inhibitor. In certain embodiments, the ATK inhibitor is a compound represented by general formula (I) or a pharmaceutically acceptable salt thereof:

Formula (I)

wherein, independently for each occurrence,
  $R^1$ is selected from hydrogen or lower alkyl; and
  $Cy^1$ is selected from substituted or unsubstituted aryl, substituted or unsubstituted heteroaryl, and substituted or unsubstituted heterocyclyl,
  provided that $Cy^1$ is not unsubstituted pyrid-4-yl.

BRIEF DESCRIPTION OF THE DRAWINGS

FIG. 5 shows the effects of certain compounds of the invention on certain metabolite levels in the MPTP model for Parkinson's disease.

3

Figure 7:
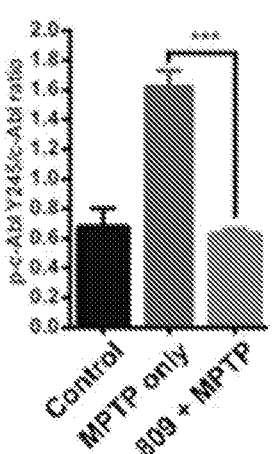
Figure 7:
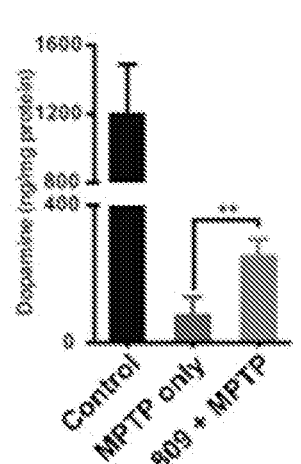
Figure 7:
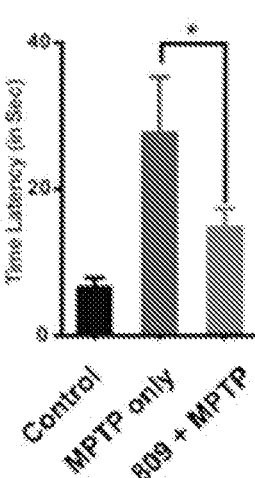

FIG. 7 shows results from the MPTP model regarding (left) the effects of Compound 809 on c-Abl phosphorylation levels in the ventral midbrain; (center) the effects of Compound 809 on dopamine levels; and (right) the effects of Compound 809 on pole test latency.

DETAILED DESCRIPTION OF THE INVENTION

In one aspect, the invention relates to compounds represented by formula (I) or a pharmaceutically acceptable salt thereof:

Formula (I)

wherein, independently for each occurrence, $R^1$ is selected from hydrogen or lower alkyl; and $Cy^1$ is selected from substituted or unsubstituted aryl, substituted or unsubstituted heteroaryl, and substituted or unsubstituted heterocyclyl, provided that $Cy^1$ is not unsubstituted pyrid-4-yl.

In certain embodiments, $Cy^1$ is selected from:

wherein, independently for each occurrence, $R^2$ and $R^3$ are selected from hydrogen, alkyl, amino, monoalkylamino, dialkylamino, cycloalkyl, halo, cyano, alkoxy, —C(O)OH, and —C(O)N($R^4$)($R^4$);

n is 1, 2, 3 or 4;

X is C($R^4$)$_2$, S, O, or N$R^4$;

$R^4$ is selected from hydrogen and substituted or unsubstituted alkyl, aralkyl, cycloalkyl, heterocyclyl, aryl, heteroaryl, heteroaralkyl, cycloalkylalkyl, or heterocyclylalkyl.

In certain embodiments, $Cy^1$ is selected from:

wherein, independently for each occurrence, $R^1$, each independently, is selected from hydrogen or lower alkyl;

$R^2$ and $R^3$ are selected from hydrogen, alkyl, amino, monoalkylamino, dialkylamino, cycloalkyl, halo, cyano, alkoxy, —C(O)OH, and —C(O)N($R^4$)($R^4$);

$R^4$ is selected from hydrogen and substituted or unsubstituted alkyl, aralkyl, cycloalkyl, heterocyclyl, aryl, heteroaryl, heteroaralkyl, cycloalkylalkyl, or heterocyclylalkyl.

In certain embodiments, $Cy^1$ is not substituted or unsubstituted pyrid-4-yl.

In certain embodiments, $Cy^1$ is not unsubstituted pyrid-4-yl or unsubstituted phenyl.

In certain embodiments, $Cy^1$ is not substituted or unsubstituted pyrid-4-yl or substituted or unsubstituted phenyl.

In certain embodiments, $Cy^1$ is 5-membered heteroaryl, aryl or heterocyclyl.

In certain embodiments, Cy$^1$ is selected from:

6

-continued

In certain embodiments, Cy$^1$ is selected from:

In certain embodiments, Cy$^1$ is selected from:

In certain embodiments, Cy$^1$ is selected from:

-continued

In certain embodiments, $R^1$ is selected from hydrogen or lower alkyl, which may optionally be deuterated. In certain preferred embodiments, $R^1$ is methyl, e.g., —$CH_3$, —$CDH_2$, —$CD_2H$, or —$CD_3$.

In one aspect, the invention relates to compounds of formula (II) or their pharmaceutically acceptable salts. These compounds were also described in U.S. Patent Application Publication No. 2014/0100225, which is hereby incorporated herein by reference (II)

wherein:

A and B are independently selected from absent, H or a moiety of Formula (II), with the proviso that at least one of A and B is a moiety of Formula (III);

(III)

wherein:

R and $R^1$ are each independently selected from H, alkenyl, alkynyl, alkoxy, aryl, heteroaryl, $C_1$-$C_8$ alkyl and $C_3$-$C_7$ cycloalkyl, wherein in each of the $C_1$-$C_8$ alkyl and $C_3$-$C_7$ cycloalkyl optionally up to three carbon atoms are replaced by a heteroatom group independently selected from O, $NR^4$, S, SO and $SO_2$ (i.e., thereby making a heteroalkyl or heterocyclyl substituent), and wherein the $C_1$-$C_8$ alkyl and $C_3$-$C_7$ cycloalkyl are each optionally substituted with from 1 to 4 $C_1$-$C_8$ alkyl, alkoxy, aryl and heteroaryl substituents; or R and $R^1$ taken together with the atom to which they are attached form a 3- to 7-membered ring, wherein the 3- to 7-membered ring optionally contains up to two heteroatom groups selected from O, $NR^4$, S, SO and $SO_2$, and is optionally substituted with 1 to 4 alkoxy, F or Cl substituents;

Y is selected from $R^2$, $OR_2$, $NH_2$, $NHR_2$, and $NR^2R^3$;

$R^2$ is selected from alkoxy, aryl, heteroaryl, $C_1$-$C_8$ alkyl and $C_3$-$C_7$ cycloalkyl, wherein in each of the $C_1$-$C_8$alkyl and $C_3$-$C_7$ cycloalkyl optionally up to three carbon atoms are replaced by a heteroatom group independently selected from O, $NR^4$, S, SO and $SO_2$ (i.e., thereby making a heteroalkyl or heterocyclyl substituent), and wherein the $C_1$-$C_8$ alkyl and $C_3$-$C_7$ cycloalkyl are each optionally substituted with from 1 to 4 $C_1$-$C_8$ alkyl, alkoxy, aryl or heteroaryl substituents;

$R^3$ is selected from alkoxy, aryl, heteroaryl, $C_1$-$C_8$ alkyl and $C_3$-$C_7$ cycloalkyl, wherein in each of the $C_1$-$C_8$ alkyl and $C_3$-$C_7$ cycloalkyl optionally up to three carbon atoms are replaced by a heteroatom group independently selected from O, $NR^4$, S, SO and $SO_2$ (i.e., thereby making a heteroalkyl or heterocyclyl substituent), and wherein the $C_1$-$C_8$ alkyl and $C_3$-$C_7$ cycloalkyl are each optionally substituted with from 1 to 4 $C_1$-$C_8$ alkyl, alkoxy, aryl or heteroaryl; or $R^2$ and $R^3$ may be taken together with the nitrogen atom to which they are attached to form a 3- to 7-membered ring, wherein the 3- to 7-membered ring optionally contains up to three heteroatom groups selected from O, $NR^4$, S, SO and $SO_2$, and is optionally substituted with alkoxy, F or Cl;

$R^4$ is, independently for each occurrence, selected from H or $C_1$-$C_8$ alkyl; and X and $X^1$ are each independently an anion or absent, provided that X is absent only when A is absent, and $X^1$ is absent only when B is absent.

In some embodiments, R and $R^1$ are each independently selected from H and $C_1$-$C_8$ alkyl, such as H or methyl. Preferably both R and $R^1$ are H.

In some embodiments, $R^2$ and $R^3$ are independently selected from $C_1$-$C_8$ alkyl and aralkyl. In some such embodiments, $R^2$ and $R^3$ are independently selected from methyl, ethyl, isopropyl, tert-butyl, isobutyl, sec-butyl, 3-methylbut-2-yl, 1-phenylethyl, benzyl or cyclobutyl.

In some embodiments, $R^4$, independently for each occurrence, is selected from H and $C_1$-$C_8$ alkyl.

In some embodiments, X and $X^1$ are each independently halide or sulfonate, such as mesylate and iodide.

Because anions are not covalently attached to the molecule, it should be understood that X and $X^1$ are not necessarily located proximal to the atom bearing A or B, and should be viewed as interchangeable within any given molecule when both are present.

In some embodiments, A is H and B is a moiety of Formula (III).

In some embodiments, A is a moiety of Formula (III) and B is H.

In other embodiments, A is a moiety of Formula (III) and B is absent.

In yet other embodiments, A is absent and B is a moiety of Formula (III).

In certain embodiments, neither A nor B is

The compounds of formula III may be divided in three classes i.e. Type I, where Y=OR$_2$; Type II, where Y=R$^2$ and Type III, where Y=NR$^2$R$^3$, wherein R$^2$ and R$^3$ are as defined above. In some embodiments, formula III is selected from the moieties that would remain after displacing chlorine from the reagents listed below:

Type I Reagents
i. chloromethyl isopropyl carbonate
ii. benzyl chloromethyl carbonate
iii. chloromethyl morpholinomethyl carbonate
iv. chloromethyl isobutyl carbonate
v. chloromethylmethyl carbonate
vi. (S)-sec-butyl chloromethyl carbonate
vii. (R)-sec-butyl chloromethyl carbonate
viii. chloromethyl((3S,5R)-3,5-dimethylmorpholino) methyl carbonate
ix. chloromethyl 2-methylcyclopropyl carbonate
x. chloromethyl2-methoxyethyl carbonate
xi. chloromethyl propyl carbonate
xii. chloromethyl cyclobutyl carbonate
xiii. chloromethyl cyclopropyl carbonate
xiv. chloromethyl 2,2-dimethylcyclobutyl carbonate
xv. chloromethyl cyclopentyl carbonate
xvi. chloromethyl oxetan-3-yl carbonate
xvii. (S)-chloromethyl tetrahydrofuran-3-yl carbonate
xviii. chloromethyl cyclohexylmethyl carbonate
xix. chloromethyl 3-methoxycyclohexyl carbonate
XX. (R)-chloromethyl tetrahydrofuran-3-yl carbonate
xxi. chloromethyl ethoxymethyl carbonate
xxii. chloromethyl oxepan-4-yl carbonate
xxiii. (1R,2S,4S)-bicyclo[2.2.1]heptan-2-yl chloromethyl carbonate
xxiv. chloromethyl 2,3-dihydro-1H-inden-1-yl carbonate
xxv. benzyl chloromethyl carbonate
xxvi. (S)-chloromethyl 1-phenylethyl carbonate
xxvii. chloromethyl cyclohexyl carbonate
xxviii. chloromethyl isobutyl carbonate
xxix. chloromethyl 4-methylcyclohexyl carbonate
xxx. chloromethyl 2-(methylthio)ethyl carbonate
xxxi. chloromethyl 3-methylcyclohexyl carbonate
xxxii. chloromethylpentan-2-yl carbonate
xxxiii. chloromethyl neopentyl carbonate
xxxiv. methyl 1-((chloromethoxy)carbonyloxy)cyclopropanecarboxylate
xxxv. chloromethyl cyclopropylmethyl carbonate
xxxvi. chloromethyl 2,2-diethoxyethyl carbonate
xxxvii. chloromethyl cyclopentylmethyl carbonate
xxxviii. methyl 2-((chloromethoxy)carbonyloxy)propanoate
xxxix. (S)-chloromethyl 2,2,4-trimethylcyclopent-3-enyl carbonate
xl. chloromethyl 1,3-dioxolan-2-yl carbonate
xli. chloromethyl(2,6-dimethylcyclohexyl)methyl carbonate
xlii. chloromethyl 2-(tetrahydro-2H-pyran-2-yl)ethyl carbonate
xliii. chloromethyl(tetrahydro-2H-pyran-4-yl)methyl carbonate xliv. chloromethyl tetrahydro-2H-pyran-4-yl carbonate
xlv. chloromethyl 1-methylcyclopentyl carbonate
xlvi. chloromethyl 1-cyclopentylethyl carbonate
xlvii. chloromethyl 3-methylcyclopentyl carbonate
xlviii. chloromethyl 3,3-dimethylcyclohexyl carbonate
xlix. chloromethyl 2,5-dimethylcyclohexyl carbonate
l. chloromethyl 1-(4-methylcyclohexyl)ethyl carbonate
li. chloromethyl(3-methyloxetan-3-yl)methyl carbonate
lii. chloromethyl(3-methyloxetan-3-yl)methyl carbonate
liii. chloromethyl 2-isopropoxyethyl carbonate
liv. (chloromethyl carbonic) 5-((3aS,4S,6aR)-2-oxohexa-hydro-1H-thieno[3,4-d]imidazol-4-yl)pentanoic anhydride
lv. 4-((chloromethoxy)carbonyloxy)-2-hydroxy-4-oxobutanoic acid
lvi. chloromethyl 4-formyl-2-methoxyphenyl carbonate
lvii. chloromethyl 3-oxobutan-2-yl carbonate
lviii. methyl 4-((chloromethoxy)carbonyloxy)benzoate
lix. (R)-2-amino-3-((chloromethoxy)carbonyloxy)propanoic acid
lx. 3-tert-butyl-4-methoxyphenyl chloromethyl carbonate
lxi. (R)-2-amino-3-(4-((chloromethoxy)carbonyloxy)phenyl)propanoic acid
lxii. (R)-2-amino-4-((chloromethoxy)carbonyloxy)-4-oxobutanoic acid
lxiii. (E)-chloromethyl 3,7-dimethylocta-2,6-dienyl carbonate
lxiv. methyl 4-((chloromethoxy)carbonyloxy)benzoate
lxv. chloromethyl 2-(4-methylcyclohex-3-enyl)propan-2-yl carbonate
lxvi. chloromethyl 3,7-dimethylocta-1,6-dien-3-yl carbonate
lxvii. 4-allyl-2-methoxyphenyl chloromethyl carbonate
lxviii. chloromethyl(1R,2S,5R)-2-isopropyl-5-methylcyclohexyl carbonate
lxix. propyl 4-((chloromethoxy)carbonyloxy)benzoate
lxx. (E)-chloromethyl 3,7-dimethylocta-2,6-dienyl carbonate Type II Reagents
i. chloromethyl cyclohexanecarboxylate
ii. chloromethyl 2-cyclohexylacetate
iii. chloromethyl 4-methylcyclohexanecarboxylate
iv. chloromethyl 1-methylcyclohexanecarboxylate
v. chloromethyl cyclopentanecarboxylate
vi. chloromethyl 1-(trifluoromethyl)cyclopentanecarboxylate
vii. chloromethyl cyclobutanecarboxylate
viii. chloromethyl 2-ethylhexanoate
ix. chloromethyl 3-cyclopentylpropanoate
X. chloromethyl cyclopropanecarboxylate
xi. chloromethyl pentanoate
xii. chloromethyl 2-methylpentanoate
xiii. chloromethyl 3,5,5-trimethylhexanoate
xiv chloromethyl 2,2-dimethylbutanoate
xv. chloromethyl 2-methylbutanoate
xvi. chloromethyl hexanoate
xvii. chloromethyl 2-ethylbutanoate
xviii. chloromethyl butyrate
xix. chloromethyl 3-phenylpropanoate
xx. chloromethyl 2-phenylpropanoate
xxi. (R)-chloromethyl 2-phenylpropanoate
xxii. (S)-chloromethyl 2-phenylpropanoate
xxiii. (1r,4r)-chloromethyl 4-methylcyclohexanecarboxylate
xxiv. chloromethyl 4-methoxycyclohexanecarboxylate
xxv. chloromethyl 4,4-difluorocyclohexanecarboxylate
xxvi. chloromethyl 3-methoxycyclohexanecarboxylate xxvii. (2R)-chloromethyl 2-methylcyclopentanecarboxylate xxviii. (R)-chloromethyl 2-methylbutanoate xxix. (S)-chloromethyl 2-methylbutanoate xxx. (S)-chloromethyl 2-methoxy-2-phenylacetate xxxi. (S)-chloromethyl 2-phenylpropanoate xxxii. (S)-chloromethyl 2-phenylbutanoate xxxiii. (S)-chloromethyl 3-phenylbutanoate xxxiv. bis(chloromethyl) 2,2-dimethylmalonate xxxv. bis(chloromethyl) oxalate xxxvi. chloromethyl 2-cyclopropylacetate xxxvii. chloromethyl 2-cyclobutylacetate xxxviii. chloromethyl 2-cyclopentylacetate xxxix. chloromethyl 2-(tetrahydrofuran-3-yl)acetate xl. chloromethyl 2-(tetrahydro-2H-pyran-4-yl)acetate xli. chloromethyl 2-methylcyclopropanecarboxylate xlii. chloromethyl 2-(1-methylcyclobutyl)acetate xliii. chloromethyl 2-(1-methylcyclopropyl)'acetate xliv. chloromethyl propionate xlv. chloromethyl acetate xlvi. chloromethyl isobutyrate xlvii. chloromethyl 2-isopropyl-3-methylbutanoate xlviii. chloromethyl 3,5-dimethylcyclohexanecarboxylate xlix. chloromethyl 2-propylpentanoate l. chloromethyl 4-methoxybenzoate li. chloromethyl 4-methylbenzoate lii. chloromethyl 3-methylbenzoate liii. chloromethyl 2,2,2-trifluoroacetate liv. chloromethyl 5,5-dimethyl-3-oxohexanoate lv. bis(chloromethyl)cyclopropane-1,1-dicarboxylate lvi. chloromethyl 1,2-dihydrocyclobutabenzene-1-carboxylate lvii. chloromethyl 2-cyclopentenylacetate lviii. chloromethyl 2-phenylbutanoate lix. chloromethyl 2,2-difluoroacetate lx. chloromethyl 4-fluorobenzoate lxi. chloromethyl 3-cyclohexylpropanoate lxii. chloromethyl 2-cyclohexylacetate lxiii. chloromethyl 3-(tetrahydro-2H-pyran-4-yl)propanoate lxiv. chloromethyl 2-(tetrahydro-2H-pyran-3-yl)acetate lxv. chloromethyl 3-(tetrahydro-2H-pyran-3-yl)propanoate lxvi. chloromethyl nicotinate Type III Reagents i. chloromethyl isopropylcarbamate ii. chloromethyl diisopropylcarbamate iii. chloromethyl dimethylcarbamate iv. chloromethyl isobutylcarbamate v. chloromethyl methylcarbamate vi. chloromethyl ethyl(isopropyl)carbamate vii. chloromethylisobutyl(methyl)carbamate viii. (S)-chloromethyl sec-butylcarbamate ix. chloromethyl methylcarbamate X. chloromethyl isopropyl(methyl)carbamate xi. chloromethyl propylcarbamate xii. chloromethyl 2-methoxyethylcarbamate xiii. chloromethyl methyl(propyl)carbamate xiv. chloromethyl diisobutylcarbamate xv. chloromethyl tert-butyl(isopropyl)carbamate xvi. chloromethyl di-sec-butylcarbamate xvii. chloromethyl aziridine-1-carboxylate xviii. chloromethyl 2-methylcyclopropylcarbamate xix. chloromethyl cyclopropylcarbamate xx. chloromethyl cyclopropylmethyl(propyl)carbamate xxi. chloromethyl cyclopropyl(methyl)carbamate xxii. chloromethyl azetidine-1-carboxylate xxiii. chloromethyl cyclobutylcarbamate xxiv. chloromethyl 2,2-dimethylcyclobutylcarbamate xxv. chloromethyl 3-methoxyazetidine-1-carboxylate xxvi. chloromethyl cyclobutyl(methyl)carbamate xxvii. chloromethyl oxetan-3-ylcarbamate xxviii. (S)-chloromethyl 2-methylpyrrolidine-1-carboxylate xxix. chloromethyl cyclopentylcarbamate xxx. chlorometh1 cyclopentyl(methyl)carbamate xxxi. chloromethyl tetrahydrofuran-3-ylcarbamate xxxii. chloromethyl piperidine-1-carboxylate xxxiii. (2R,6S)-chloromethyl 2,6-dimethylpiperidine-1-carboxylate xxxiv. (R)-chloromethyl 2-methylpiperidine-1-carboxylate xxxv. chloromethyl piperidine-1-carboxylate xxxvi. chloromethyl 3-methoxycyclohexylcarbamate xxxvii. chloromethyl cyclohexylmethylcarbamate xxxviii. chloromethyl cyclohexylmethyl(methyl)carbamate xxxix. chloromethyl morpholine-4-carboxylate xl. (3S,5R)-chloromethyl 3,5-dimethylmorpholine-4-carboxylate xli. (3R,5S)-chloromethyl 3,5-dimethylmorpholine-4-carboxylate xlii. (2S,6R)-chloromethyl 2,6-dimethylmorpholine-4-carboxylate xliii. chloromethyl 4-methylpiperazine-1-carboxylate xliv. chloromethylazepane-1-carboxylate xlv. chloromethylcycloheptylcarbamate xlvi. chloromethyl oxepan-4-ylcarbamate xlvii. chloromethyl(1R,2S,4S)-bicyclo[2.2.1]heptan-2-yl-carbamate xlviii. chloromethyl 2,3-dihydro-1H-inden-1-ylcarbamate xlix. chloromethyl benzylcarbamate l. (S)-chloromethyl 1-phenylethylcarbamate li. ethyl 2-((chloromethoxy)carbonylamino)-3-methylbutanoate lii. ethyl 2-((chloromethoxy)carbonylamino)-3-phenylpropanoate liii. (S)-diethyl 2-((chloromethoxy)carbonylamino) pentanedioate liv. ethyl((chloromethoxy)carbonylamino)propanoate lv. ethyl 2-amino-6-((chloromethoxy)carbonylamino) hexanoate lvi. ethyl 2-((chloromethoxy)carbonylamino)-4-methylpentanoate lvii. ethyl 2-((chloromethoxy)carbonylamino)-3-methylpentanoate lviii. (S)-dimethyl 2-((chloromethoxy)carbonylamino) succinate lix. (S)-ethyl 2-((chloromethoxy)carbonylamino)-5-guanidinopentanoate lx. (S)-ethyl 4-amino-2-((chloromethoxy)carbonylamino)-4-oxobutanoate lxi. (S)-ethyl 2-amino-5-((chloromethoxy)carbonylamino)pentanoate lxii. (S)-ethyl 5-amino-2-((chloromethoxy)carbonylamino)-5-oxopentanoate lxiii. ethyl 2-((chloromethoxy)carbonylamino)-4-(methylthio)butanoate lxiv. 1-chloromethyl 3-methyl 2-methyl-5,6-dihydropyridine-1,3(2H)-dicarboxylate lxv. (S)-chloromethyl(1-methylpyrrolidin-2-yl)methyl carbonate lxvi. (R)-chloromethyl(1-methylpyrrolidin-2-yl)methyl carbonate

13 lxvii. (S)-(1-benzylpyrrolidin-2-yl)methyl chloromethyl carbonate lxviii. chloromethyl 1H-pyrrole-1-carboxylate lxix. chloromethyl 2-nicotinoylhydrazinecarboxylate lxx. (6S)-3-chloro-7-((chloromethoxy)carbonylamino)-8-oxo-5-thia-1-azabicyclo[4.2.0]oct-2-ene-2-carboxylic acid lxxi. (6S)-7-((chloromethoxy)carbonylamino)-8-oxo-3-vinyl-5-thia-1-azabicyclo[4.2.0]oct-2-ene-2-carboxylic acid lxxii. (6S)-7-((chloromethoxy)carbonylamino)-3-(methoxymethyl)-8-oxo-5-thia-1-azabicyclo[4.2.0]oct-2-ene-2-carboxylic acid lxxiii. (6R,7R)-7-((chloromethoxy)carbonylamino)-3-methoxy-8-oxo-5-thia-1-azabicyclo[4.2.0]oct-2-ene-2-carboxylic acid lxxiv. chloromethyl 3-(4-chlorophenyl)-1H-pyrazole-1-carboxylate lxxv. chloromethyl 3-(4-fluorophenyl)-1H-pyrazole-1-carboxylate lxxvi. chloromethyl 3-phenyl-1H-pyrazole-1-carboxylate lxxvii. chloromethyl 3-(4bromophenyl)-1H-pyrazole-1-carboxylate lxxviii. chloromethyl 2-cyano-1H-pyrrole-1-carboxylate lxxix. chloromethyl 4-oxopiperidine-1-carboxylate lxxx. 1-chloromethyl 3-ethyl 2-oxopiperidine-1,3-dicarboxylate lxxxi. chloromethyl 2,2,6,6-tetramethyl-4-oxopiperidine-1-carboxylate lxxxii. chloromethyl 2-oxopiperidine-1-carboxylate In some embodiments, the compounds of Formula (II) are selected from compounds of Formula (IV) or Formula (V):

Formula (IV)

Formula (V)

wherein A and B are independently selected from:

14

-continued wherein $R^5$ represents a nitrogen atom of the imatinib moiety linked to A or B, and X may be iodide, chloride, bromide, mesylate, tosylate, or any other pharmaceutically acceptable anion to provide a pharmaceutically acceptable salt.

The compounds of Formula (II) may be present as a single stereoisomer (e.g., enriched to at least 95% purity relative to the total amount of all stereoisomers present), a racemate, or a mixture of enantiomers or diastereomers in any ratio.

In some embodiments, the compound of Formula (II) is selected from the compounds listed below:

1002

1-methyl-4-(4-((4-methyl-3-((4-(pyridin-3-yl)py-rimidin-2-yl)amino)phenyl)carbamoyl)benzyl)-1-((pivaloyloxy)methyl)piperazin-1-ium iodide

1003

1-methyl-4-(4-((4-methyl-3-((4-(1-((pivaloyloxy)methyl)pyridin-1-ium-3-yl)pyrimidin-2-yl)amino)phenyl)carbamoyl)benzyl)-1-((pivaloyloxy)methyl)piperazin-1-ium diiodide

1004

16

1-methyl-4-(4-((4-methyl-3-((4-(pyridin-3-yl)py-rimidin-2-yl)amino)phenyl)carbamoyl)benzyl)-1-(((morpholine-4-carbonyl)oxy)methyl)piperazin-1-ium iodide

1005

1-(((isopropoxycarbonyl)oxy)methyl)-1-methyl-4-(4-((4-methyl-3-((4-(pyridin-3-yl)pyrimidin-2-yl)amino)phenyl)carbamoyl)benzyl)piperazin-1-ium iodide

1006

1-(((isopropoxycarbonyl)oxy)methyl)-1-methyl-4-(4-((4-methyl-3-((4-(pyridin-3-yl)pyrimidin-2-yl)amino)phenyl)carbamoyl)benzyl)piperazin-1-ium methane sulfonate

1007

1-(((isopropoxycarbonyl)oxy)methyl)-1-methyl-4-(4-((4-methyl-3-((4-(pyridin-3-yl)pyrimidin-2-yl)amino)phenyl)carbamoyl)benzyl)piperazin-1-ium p-tolyl sulfonate

1008

1-methyl-4-(4-(4-methyl-3-(4-(pyridin-3-yl)pyrimi-
din-2-ylamino)phenylcarbamoyl)benzyl)-1-((3-meth-
ylbutanoyloxy)methyl)piperazin-1-ium iodide

1009

1-((isopropylcarbamoyloxy)methyl)-1-methyl-4-(4-
(4-methyl-3-(4-(pyridin-3-yl)pyrimidin-2-ylamino)
phenylcarbamoyl)benzyl)piperazin-1-ium iodide

1010

(R)-1-methyl-4-(4-(4-methyl-3-(4-(pyridin-3-yl)
pyrimidin-2-ylamino)phenylcarbamoyl)benzyl)-1-
((((1-phenylethoxy)carbonyloxy)methyl)piperazin-1-
ium iodide

1011

(R)-1-methyl-4-(4-(4-methyl-3-(4-(pyridin-3-yl)
pyrimidin-2-ylamino)phenylcarbamoyl)benzyl)-1-
((1-phenylethylcarbamoyloxy)methyl)piperazin-1-
ium iodide

1012

(R)-1-((sec-butoxycarbonyloxy)methyl)-1-methyl-4-
(4-(4-methyl-3-(4-(pyridin-3-yl)pyrimidin-2-
ylamino)phenylcarbamoyl)benzyl)piperazin-1-ium
iodide

1013

1-(isobutyryloxymethyl)-1-methyl-4-(4-(4-methyl-3-
(4-(pyridin-3-yl)pyrimidin-2-ylamino)phenylcar-
bamoyl)benzyl)piperazin-1-ium iodide

1014

1-((benzyloxycarbonyloxy)methyl)-1-methyl-4-(4-
(4-methyl-3-(4-(pyridin-3-yl)pyrimidin-2-ylamino)
phenylcarbamoyl)benzyl)piperazin-1-ium iodide

1015

(R)-1-methyl-4-(4-(4-methyl-3-(4-(pyridin-3-yl)
pyrimidin-2-ylamino)phenylcarbamoyl)benzyl)-1-
(((1-phenylethoxy)carbonyloxy)methyl)piperazin-1-
ium iodide

1016

1-methyl-4-(4-(4-methyl-3-(4-(pyridin-3-yl)pyrimi-
din-2-ylamino)phenylcarbamoyl)benzyl)-1-(((3-
methylbutan-2-yloxy)carbonyloxy)methyl)piperazin-
1-ium iodide

1017

1-((benzyl(methyl)carbamoyloxy)methyl)-1-methyl-
4-(4-(4-methyl-3-(4-(pyridin-3-yl)pyrimidin-2-
ylamino)phenylcarbamoyl)benzyl)piperazin-1-ium
iodide

1018

(S)-1-methyl-4-(4-(4-methyl-3-(4-(pyridin-3-yl)py-
rimidin-2-ylamino)phenylcarbamoyl)benzyl)-1-((1-
phenylethylcarbamoyloxy)methyl)piperazin-1-ium
iodide

1019

1-((ethoxycarbonyloxy)methyl)-1-methyl-4-(4-(4-
methyl-3-(4-(pyridin-3-yl)pyrimidin-2-ylamino)phe-
nylcarbamoyl)benzyl)piperazin-1-ium iodide

1020

1-((cyclobutoxycarbonyloxy)methyl)-1-methyl-4-(4-
(3-methyl-4-(4-(pyridin-3-yl)pyrimidin-2-ylamino)
phenylcarbamoyl)benzyl)piperazin-1-ium iodide

1026

1-methyl-4-(4-((4-methyl-3-((4-(pyridin-3-yl)py-
rimidin-2-yl)amino)phenyl)carbamoyl)benzyl)piper-
azin-1-ium methanesulfonate (R)-1-((sec-butylcarbamoyloxy)methyl)-1-methyl-4-
(4-(4-methyl-3-(4-(pyridin-3-yl)pyrimidin-2-
ylamino)phenylcarbamoyl)benzyl)piperazin-1-ium
iodide

1027

1-((2,2-dimethylbutanoyloxy)methyl)-1-methyl-4-
(4-(4-methyl-3-(4-(pyridin-3-yl)pyrimidin-2-
ylamino)phenylcarbamoyl)benzyl)piperazin-1-ium
iodide

1030

1028

1-methyl-4-(4-(4-methyl-3-(4-(pyridin-3-yl)pyrimi-
din-2-ylamino)phenylcarbamoyl)benzyl)-1-((tert-
pentyloxycarbonyloxy)methyl)piperazin-1-ium
iodide 1-methyl-4-(4-(4-methyl-3-(4-(pyridin-3-yl)pyrimi-
din-2-ylamino)phenylcarbamoyl)benzyl)-1-((2-phe-
nylacetoxy)methyl)piperazin-1-ium iodide

1031

1029

4-(4-((3-((4-(1-((((isopropoxycarbonyl)oxy)methyl)
pyridin-1-ium-3-yl)pyrimidin-2-yl)amino)-4-meth-
ylphenyl)carbamoyl)benzyl)-1-methylpiperazin-1-
ium monoiodide monomesylate

1032

3-(2-((2-methyl-5-(4-((4-methylpiperazin-1-yl)
methyl)benzamido)phenyl)amino)pyrimidin-4-yl)-1-
(((morpholine-4-carbonyl)oxy)methyl)pyridin-1-ium
monoiodide monomesylate

| No. | Structure | IUPAC name | m/z |
|---|---|---|---|
| 1030 | | 1-methyl-4-(4-((4-methyl-3-((4-(pyridin-3-yl)pyrimidin-2-yl)amino)phenyl)carbamoyl)benzyl)-1-((2-phenylacetoxy)methyl)piperazin-1-ium iodide | 643 |
| 10737.02 | | 1-methyl-4-(4-((4-methyl-3-((4-(pyridin-3-yl)pyrimidin-2-yl)amino)phenyl)carbamoyl)benzyl)-1-((2-phenylacetoxy)methyl)piperazin-1-ium methanesulfonate | 643 |
| 10737.04 | | 1-methyl-4-(4-((4-methyl-3((4-(pyridin-3-yl)pyrimidin-2-yl)amino)phenyl)carbamoyl)benzyl)-1-((2-phenylacetoxy)methyl)piperazin-1-ium tetrafluoroborate | 643 |
| 10737.06 | | 1-methyl-4-(4-((4-methyl-3-((4-(pyridin-3-yl)pyrimidin-2-yl)amino)phenyl)carbamoyl)benzyl)-1-((2-phenylacetoxy)methyl)piperazin-1-ium trifluoromethanesulfonate | 643 |

-continued

| No. | Structure | IUPAC name | m/z |
|---|---|---|---|
| 10737.07 | | 1-methyl-4-(4-((4-methyl-3-((4-(pyridin-3-yl)pyrimidin-2-yl)amino)phenyl)carbamoyl)benzyl)-1-((2-phenylacetoxy)methyl)piperazin-1-ium nitrate | 643 |
| 10737.08 | | 1-methyl-4-(4-((4-methyl-3-((4-(pyridin-3-yl)pyrimidin-2-yl)amino)phenyl)carbamoyl)benzyl)-1-((2-phenylacetoxy)methyl)piperazin-1-ium p-toluene sulfonate | 643 |
| 11124.01 | | 1-methyl-4-(4-((4-methyl-3-((4-(pyridin-3-yl)pyrimidin-2-yl)amino)phenyl)carbamoyl)benzyl)-1-(((2-phenylpropanoyl)oxy)methyl)piperazin-1-ium iodide | 657 |
| 11124.02 | | 1-methyl-4-(4-((4-methyl-3-((4-(pyridin-3-yl)pyrimidin-2-yl)amino)phenyl)carbamoyl)benzyl)-1-(((2-phenylpropanoyl)oxy)methyl)piperazin-1-ium tetrafluoroborate | 657 |
| 11124.03 | | 1-methyl-4-(4-((4-methyl-3-((4-(pyridin-3-yl)pyrimidin-2-yl)amino)phenyl)carbamoyl)benzyl)-1-(((2-phenylpropanoyl)oxy)methyl)piperazin-1-ium methanesulfonate | 657 |

In one aspect, the invention provides a pharmaceutical composition comprising a compound as disclosed herein.

In certain embodiments, the pharmaceutical composition further comprises one or more pharmaceutically acceptable excipients.

In one aspect, the invention provides a compound or composition, as disclosed herein, for conjoint administration with one or more compounds independently selected from central nervous system drugs, such as CNS/respiratory stimulants, analgesics, narcotic agonists, narcotic antagonists, nonsteroidal anti-inflammatory/analgesic agents, behavior-modifying agents, tranquilizers/sedatives, anesthetic agents, inhalants, narcotics, reversal agents, anticonvulsants, skeletal muscle relaxants, smooth muscle relaxants, cardiovascular agents, inotropic agents, antiarrhythmic drugs, anticholinergics, vasodilating agents, agents used in treatment of shock, alpha-adrenergic blocking agents, beta-adrenergic blocking agents, respiratory drugs, bronchodilators, sympathomimetics, antihistamines, antitussives, agents for urinary incontinence/retention, urinary alkalinizers, urinary acidifiers, cholinergic stimulants, agents for urolithiasis, gastrointestinal agents, antiemetic agents, antacids, histamine H2 antagonists, gastromucosal protectants, proton pump inhibitors, appetite stimulants, GI antispasmodics-anticholinergics, GI stimulants, laxatives, saline, lubricant, surfactant, antidiarrheals, hormones/endocrine/reproductive agents, sex hormones, anabolic steroids, posterior pituitary hormones, adrenal cortical steroids, glucocorticoids, antidiabetic agents, thyroid drugs, thyroid hormones, endocrine/reproductive drugs, prostaglandins, antiinfective drugs, antiparasitics, anticoccidial agents, antibiotics, antituberculosis, aminocyclitols, cephalosporins, macrolides, penicillins, tetracyclines, lincosamides, quinolones, sulfonamides, antibacterials, antifungal agents, antiviral agents, blood modifying agents, clotting agents, anticoagulants, erythropoietic agents, antineoplastics/immunosuppressives, alkylating agents, antidotes, bone/joint agents, dermatologic agents (systemic), vitamins and minerals/nutrients, systemic acidifiers, systemic alkalinizers, anti-cancer agents, and antiviral agents.

Definitions

The term "alkyl" refers to the radical of saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g. methyl, ethyl, n-propyl, i-propyl, n-butyl and n-pentyl.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated. In preferred embodiments, a straight chain or branched chain alkenyl has 1-12 carbons in its backbone, preferably 1-8 carbons in its backbone, and more preferably 1-6 carbons in its backbone. Exemplary alkenyl groups include allyl, propenyl, butenyl, 2-methyl-2-butenyl, and the like.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated. In preferred embodiments, an alkynyl has 1-12 carbons in its backbone, preferably 1-8 carbons in its backbone, and more preferably 1-6 carbons in its backbone. Exemplary alkynyl groups include propynyl, butynyl, 3-methylpent-1-ynyl, and the like.

The term "aralkyl", as used herein, refers to an alkyl group substituted with one or more aryl groups.

The term "aryl", as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, naphthyl, biphenyl, anthracenyl and the like.

The term "cycloalkyl", as used herein, refers to the radical of a saturated aliphatic ring. In preferred embodiments, cycloalkyls have from 3-10 carbon atoms in their ring structure, and more preferably from 5-7 carbon atoms in the ring structure. Suitable cycloalkyls include cycloheptyl, cyclohexyl, cyclopentyl, cyclobutyl and cyclopropyl.

The terms "cycloalkyl" and "cycloalkenyl" refer to cyclic hydrocarbon groups of 3 to 12 carbon atoms.

The terms "halogen", "halide" and "halo", as used herein, mean halogen and include fluoro, chloro, bromo and iodo.

The terms "heterocyclyl", "heterocycle", "heterocyclo" and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The heterocyclic group may be attached at any heteroatom or carbon atom of the ring or ring system. Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like. Exemplary bicyclic heterocyclic groups include indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo [2,3-c]pyridinyl, furo[3,2-b]pyridinyl] or furo [2,3-b]pyridinyl), dihydroisoindolyl, dihydroquinazolinyl (such as 3,4-dihydro-4-oxo-quinazolinyl), tetrahydroquinolinyl and the like. Exemplary tricyclic heterocyclic groups include carbazolyl, benzindolyl, phenanthrolinyl, acridinyl, phenanthridinyl, xanthenyl and the like.

The term "heteroalkyl", as used herein, refers to a saturated or unsaturated chain of carbon atoms including at least one heteroatom (e.g., O, S, or $NR^4$, such as where $R^4$ is H or lower alkyl).

The term "heteroaryl" includes substituted or unsubstituted aromatic single ring structures, preferably 5- to 7-membered rings, more preferably 5- to 6-membered rings, whose ring structures include at least one heteroatom (e.g., O, N, or S), preferably one to four or one to 3 heteroatoms, more preferably one or two heteroatoms. When two or more heteroatoms are present in a heteroaryl ring, they may be the same or different. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Preferred polycyclic ring systems have two cyclic rings in which both of the rings are aromatic. Exemplary heteroaryl groups include pyrrolyl, pyrazolyl, imidazolyl, oxazolyl, isoxazolyl, thiazolyl, thiadiazolyl, isothiazolyl, furyl, thienyl, oxadiazolyl, pyridinyl, pyrazinyl, pyrimidinyl, quinolinyl, pyridazinyl, triazolyl, triazinyl, and the like.

The term "alkoxy" is intended to mean an alkyl radical, as defined herein, attached directly to an oxygen atom. Some embodiments are 1 to 5 carbons, some embodiments are 1 to 4 carbons, some embodiments are 1 to 3 carbons and some embodiments are 1 or 2 carbons. Examples include methoxy, ethoxy, n-propoxy, isopropoxy, n-butoxy, tert-butoxy, 5-isobutoxy, sec-butoxy, and the like.

The term "heteroatom", as used herein, means an atom of any element other than carbon or hydrogen. Preferred heteroatoms are nitrogen, oxygen, and sulfur.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

Unless specifically stated as "unsubstituted," references to chemical moieties herein are understood to include substituted variants. For example, reference to an "aryl" group or moiety implicitly includes both substituted and unsubstituted variants. Similarly, references to elements are understood to include any suitable isotope of that element. Thus, for example, a hydrogen substituent could be protium, deuterium, or tritium, or a carbon atom could be $^{12}$C, $^{13}$C, or $^{14}$C. In certain embodiments of the compounds disclosed herein, certain atoms may be isotopically enriched, e.g., for radioisotopic labelling or for a metabolically beneficial isotope effect (e.g., by isotopically enriching for deuterium at a hydrogen substituent). In such embodiments, the compound may be isotopically enriched for the desired isotope such that at least 15%, at least 25%, at least 50%, at least 60%, at least 75%, or even at least 90% more of the molecules of the compound in the composition have the desired isotope at the indicated position.

The term "unsaturated ring" includes partially unsaturated and aromatic rings.

As used herein, the term "tumoral disease" refers to a hyperproliferative disease, such as cancer.

As used herein, the term "conjoint administration" means administration of two or more agents to a subject of interest as part of a single therapeutic regimen. The administration(s) can be either simultaneous or sequential, i.e., administering one agent followed by administering of a second (and/or a third one, etc.) at a later time, as long as the agents administered co-exist in the subject being treated, or at least one agent will have the opportunity to act upon the same target tissues of other agents while said target tissues are still under the influence of said other agents. In a certain embodiment, agents to be administered can be included in a single pharmaceutical composition and administered together. In a certain embodiment, the agents are administered simultaneously, including through separate routes. In a certain embodiment, one or more agents are administered continuously, while other agents are administered only at predetermined intervals (such as a single large dosage, or twice a week at smaller dosages, etc.).

The present invention includes within its scope the salts and isomers. Compounds of the present invention may in some cases form salts, which are also within the scope of this invention. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds may be formed, for example, by reacting a compound with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxy ethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts (formed, for example, wherein the substituent comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the invention are also contemplated herein. Solvates of the compounds of formula I are preferably hydrates or other pharmaceutically acceptable solvates.

All stereoisomers of the present compounds, such as those which may exist due to asymmetric carbons on the R substituents of the compound, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention may have the S or R configuration.

As used herein, the term "treating" or "treatment" includes reversing, reducing, or arresting the symptoms, clinical signs, and underlying pathology of a condition in manner to improve or stabilize a subject's condition. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The present application also envisages within its scope the effect of selection of suitable counterions. The counterion of the compounds of the present invention may be chosen by selecting the dissociation constant for the drug capable of ionization within the said pH range. By estimating the ionized and un-ionized drug concentration of any compound (using well established equations such a Henderson-Hasselbach equation), the solubility and consequently the absorption of the drug may be altered.

The compounds generated may be present as a single stereoisomer (e.g., enriched to at least 95% purity relative to the total amount of all stereoisomers present), a racemate, or a mixture of enantiomers or diastereomers in any ratio.

Pharmaceutical Compositions

The present invention further provides pharmaceutical compositions comprising a compound of formula (I) or (II) or its pharmaceutically acceptable salt thereof as an active ingredient along with pharmaceutically acceptable additives/excipients/adjuvants/vehicles.

Compounds of the present invention may be used in a pharmaceutical composition, e.g., combined with a pharmaceutically acceptable carrier, for administration to a patient. Such a composition may also contain diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. Such additional factors and/or agents may be included in the pharmaceutical composition to produce a synergistic effect with compounds of the invention, or to minimize side effects caused by the compound of the invention.

The pharmaceutical compositions of the invention may be in the form of a liposome or micelles in which compounds of the present invention are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The composition may be administered in a variety of ways including orally, nasally, buccally, sublingually, intravenously, transmucosally, parenterally, by inhalation, spray, transdermally, subcutaneously, intrathecally, topically or rectally and may be formulated according to methods known in the art.

The effective dosage form for a mammal may be about 0.1-100 mg/kg of body weight of active compound, which may be administered as a single dose or in the form of individual doses, such as from 1 to 4 times a day.

The mammal may be an adult human.

The compounds of the present invention may optionally be administered with one or more additional agents. Exemplary additional agents include one or more compounds independently selected from central nervous system drugs, such as CNS/respiratory stimulants, analgesics, narcotic agonists, narcotic antagonists, nonsteroidal anti-inflammatory/analgesic agents, behavior-modifying agents, tranquilizers/sedatives, anesthetic agents, inhalants, narcotics, reversal agents, anticonvulsants, skeletal muscle relaxants, smooth muscle relaxants, cardiovascular agents, inotropic agents, antiarrhythmic drugs, anticholinergics, vasodilating agents, agents used in treatment of shock, alpha-adrenergic blocking agents, beta-adrenergic blocking agents, respiratory drugs, bronchodilators, sympathomimetics, antihistamines, antitussives, agents for urinary incontinence/retention, urinary alkalinizers, urinary acidifiers, cholinergic stimulants, agents for urolithiasis, gastrointestinal (GI) agents, antiemetic agents, antacids, histamine H2 antagonists, gastromucosal protectants, proton pump inhibitors, appetite stimulants, GI antispasmodics-anticholinergics, GI stimulants, laxatives, saline, bulk producing, lubricant, surfactant, antidiarrheals, hormones/endocrine/reproductive agents, sex hormones, anabolic steroids, posterior pituitary hormones, adrenal cortical steroids, glucocorticoids, antidiabetic agents, thyroid drugs, thyroid hormones, misc. endocrine/reproductive drugs, prostaglandins, antiinfective drugs, antiparasitics, anticoccidial agents, antibiotics, antituberculosis, aminocyclitols, cephalosporins, macrolides, penicillins, tetracyclines, lincosamides, quinolones, sulfonamides, antibacterials, antifungal agents, antiviral agents, blood modifying agents, clotting agents, anticoagulants, erythropoietic agents, antineoplastics/immunosuppressives, alkylating agents, antidotes, bone/joint agents, dermatologic agents (systemic), vitamins and minerals/nutrients, systemic acidifiers, systemic alkalinizers, anti-cancer agents, and anti-viral agents.

Methods of Use

The present invention further provides a method of prophylaxis and/or treatment of, and/or ameliorating the symptoms of, diseases, comprising administering a therapeutically effective amount of a compound of formula (I) or (II) or pharmaceutically acceptable salts thereof or pharmaceutical compositions comprising the compound of formula (I) or (II) as the active ingredient.

Methods of Treating Parkinson'S Disease

In one aspect, the present invention provides methods of treating, inhibiting, or preventing Parkinson's disease or its symptoms comprising administering to a subject in need thereof a therapeutically effective amount of an Abelson-family tyrosine kinase (ATK) inhibitor. In some embodiments, the methods comprise administering a pharmaceutical composition comprising an ATK inhibitor as described herein.

In some embodiments, the ATK inhibitor is a compound of formula (I). In certain preferred embodiments, the ATK inhibitor is selected from Compound 207, 832, 8270, or 809.

In some embodiments, the ATK inhibitor is a compound of formula (II).

In some embodiments of this aspect, the ATK inhibitor is selected from bafetinib, dasatinib, flumatinib, imatinib, metatinib, nilotinib, pexmetinib, ponatinib, rebastinib, tozasertib, XL228, ON 146040, TG100598, SUN-K706, SUN-K954, SGX393, SAR103168, PHA680626, ON044580, ON012380, NRCAN019, LS104, KW2449, HM95091, AT9283, AEG41174, ACTB1011, or ACTB1011, or their pharmaceutically acceptable salts. In preferred embodiments, the ATK inhibitor is selected from imatinib, nilotinib, dasatinib, or bafetinib, or their pharmaceutically acceptable salts.

The ATK inhibitor may be administered by any route known to those of skill in the art. In certain preferred embodiments, the ATK inhibitor or pharmaceutical composition is administered orally, nasally, buccally, sublingually, intravenously, transmucosally, parenterally, by inhalation, spray, transdermally, subcutaneously, topically or rectally. In certain preferred embodiments, the ATK inhibitor or pharmaceutical composition is administered orally.

Exemplification

The invention now being generally described, it will be more readily understood by reference to the following examples, which are included merely for purposes of illustration of certain aspects and embodiments of the present invention, and are not intended to limit the invention.

Example 1: Synthetic Protocols

Scheme 1 Synthesis of Intermediates 5 and 6

-continued

5

6

Synthesis of (E)-1-(5-bromopyridin-3-yl)-3-(dimethylamino)prop-2-en-1-one (2)

A solution of 1 (40.0 g, 200 mmol) and R-1 (119.0 g, 1000 mmol) in 500 mL of THF was stirred at 70° C. overnight. TLC indicated the reaction was completed. The mixture was cooled to room temperature and removed the solvent at reduced pressure. The resulting solid was washed with hexane to afford 2 as a yellow solid (47.2 g, 93%).

Synthesis of 4-(5-bromopyridin-3-yl)-N-(2-methyl-5-nitrophenyl)pyrimidin-2-amine (3)

A mixture of 2 (45 g, 176.5 mmol), 7 (40.6 g, 159.2 mmol), $K_2CO_3$ (44.0 g, 318.8 mmol) in 500 mL of n-BuOH was heated at 120° C. for 16 hours. The reaction mixture was filtered, and the solvent was removed at reduced pressure.

The residue was purified by chromatography column (silica gel, eluted with petroleum ether (PE)/ethyl acetate (EA), PE/EA=2:1) to afford 3 (47.0 g, 70%) was a light yellow solid.

Synthesis of N'-(4-(5-bromopyridin-3-yl)pyrimidin-2-yl)-6-methylbenzene-1,3-diamine (4)

A solution of 3 (45.0 g, 116.9 mmol) and $SnCl_2$ (132.0 g, 585 mmol) in 300 mL of EtOAc was heated to reflux overnight, then the reaction was cooled to room temperature, filtered and the solution was concentrated at reduced pressure to afford 4 (44.0 g, 100%). It was directly used for the next step without any further purification.

Synthesis of N-(3-(4-(5-bromopyridin-3-yl)pyrimidin-2-ylamino)-4-methylphenyl)-4-((4-methylpiperazin-1-yl)methyl)benzamide (5)

The above crude 4 (30.0 g, 84.5 mmol) and 8 (40.0 g, 123.0 mmol) were dissolved in 300 mL of i-BuOH, then the resulting solution was warmed to 80° C. for about 5 hours, after completion of the reaction, the mixture was cooled to room temperature, and removed the solvent under reduced pressure. The resulting residue was purified by flash chromatography on silica gel (Hexane/EA=2:1) to afford 5 (45.0 g, 93%) as a yellow solid.

Synthesis of 5-(2-(2-methyl-5-(4-((4-methylpiperazin-1-yl)methyl)benzamido)phenylamino)pyrimidin-4-yl)pyridin-3-ylboronic acid (6)

A mixture of 5 (10.0 g, 17.5 mmol), KOAc (2.8 g, 28.1 mmol), PCy$_3$ (0.3 g, 1.1 mmol), Pd$_2$(dba)$_3$ (0.4 g, 0.5 mmol) and 4,4,4',4',5,5,5',5'-octamethyl-2,2'-bi (1,3,2-dioxaborolane) (7.1 g, 28.0 mmol) in dioxane (150 mL), was stirred at 80° C. overnight, after completion of the reaction. The reaction solution was removed at reduced pressure to afford crude 6 (11.0 g, yield 100%) as yellow solid. It was directly used for next step without further purification.

Scheme 2: Synthesis of Intermediates 7, 8 and 9

Pd(PPh$_3$)$_4$, TEA, dioxane, 100° C., o/n

5

NaH (70%), THF, reflux

7

-continued

NH2NH2, EtOH, reflux, 1 h

8

HATU, CH3COONH4 or CH3NH2 or (CH3)2NH

DIPEA, DMF, r.t., 3 h

9

Synthesis of N-(3-(4-(5-acetylpyridin-3-yl)pyrimi-
din-2-ylamino)-4-methylphenyl)-4-((4-methylpiper-
azin-1-yl)methyl)benzamide (7)

A solution of 5 (1.1 g, 2.0 mmol), tributyl(1-ethoxyvinyl)
stannane (0.9 g, 2.6 mmol), Pd(PPh₃)₄ (0.2 g, 0.1 mmol) and
triethylamine (0.3 g, 3.0 mmol) in degassed dioxane (50 mL)
was heated to reflux for 24 hours. The solvent was then
evaporated in vacuo and the residue was filtered through a
thick pad of SiO₂. The solid obtained was taken up in dry
THF (60 ml), cooled to 0° C., and treated with 1N HCl. The
solution was stirred for 2 hours at room temperature and then
neutralized with sat. aq. NaHCO₃. The mixture was
extracted with EA and the organic layers were washed with
brine, dried over Na₂SO₄, and concentrated in vacuo. The
residue was purified by flash chromatography (silica gel,
eluted with PE/EA=2:1) to afford 7 (1.0 g, 94%) as a white
solid.

Synthesis of ethyl 4-(5-(2-(2-methyl-5-(4-((4-meth-
ylpiperazin-1-yl)methyl)benzamido)phenylamino)
pyrimidin-4-yl)pyridin-3-yl)-2,4-dioxobutanoate (8)

Diethyl oxalate (0.4 g, 2.3 mmol) was added to a suspen-
sion of sodium hydride (70 percent, 0.2 g) in 15 mL of
tetrahydrofuran, and refluxed for about 15 min. Then a
solution of 7 (1.0 g, 1.9 mmol) in 5 mL of tetrahydrofuran
was added dropwise over 30 min, and refluxed for 90 min.
After cooling down, the reaction mixture was poured into
ice-cold water, which was neutralized with diluted hydro-
chloric acid and extracted with ethyl acetate, dried over
Na₂SO₄, and concentrated. The crude product 8 (0.8 g, 67%)
was used for the next step without any further purification.

Synthesis of 5-(5-(2-(2-methyl-5-(4-((4-methylpip-
erazin-1-yl)methyl)benzamido)phenylamino)pyrimi-
din-4-yl)pyridin-3-yl)-4H-pyrazole-3-carboxylic
acid (9)

To a solution of 8 (0.8 g, 1.26 mmol) in 20 mL of EtOH,
hydrazine (0.1 g, 2.54 mmol) was added. The resulting
mixture was heated to reflux for 60 min. The solution was
removed under reduced pressure, and the residue was puri-
fied by prep-HPLC (basic) to afford 9 (0.6 g, 78%) as a white
solid.

Synthesis of Library Compounds

R =

-continued

118

119

200

201

202

203

207

303

304

305

-continued

306

308

309

401

402

403

404

405

General procedure: A solution of 9 (160 mg, 0.26 mmol), HATU (148 mg, 0.39 mmol), $R_1R_2NH$ (1.2 e.q.) and DIPEA (70 mg, 0.54 mmol) in 2 mL of DMF was stirred for 3 hours at room temperature. The resulting mixture was evaporated under reduced pressure and the residue was purified by prep-HPLC to afford desired library compounds.

HATU, $R_1R_2NH$

DIPEA, DMF, r.t., 3 h

9

Compounds 115, 116 and 117 were prepared using this general procedure.

General procedure: A mixture of 5 (200 mg, 0.35 mmol), $RB(OH)_2$ (2.0 eq.), $Pd(PPh_3)_4$ (40 mg, 0.03 mmol), $Na_2CO_3$ (112 mg, 1.05 mmol) in dioxane (4 mL) and water (1 mL), The resulting reaction mixture was irradiated for 90 min in a microwave oven. Then the reaction mixture was cooled to room temperature and concentrated at reduced pressure. The residue was purified by prep-HPLC to afford desired library compounds as a solid.

$RB(OH)_2$, $Pd(PPh_3)_4$, $NaCO_3$ dioxane/$H_2O$, 100° C., MW

5

-continued

Compounds 101, 102, 103, 118, 201, 202, 309, 401, 402, 403, 404 and 405 were prepared using this general procedure.

General procedure: A mixture of 6 (150 mg, 0.34 mmol), RBr or RI (2.0 eq.), Pd(dppf)Cl$_2$ (57 mg, 0.07 mmol), Cs$_2$CO$_3$ (280 mg, 0.85 mmol) in i-PrOH (4 mL) and water (1 mL) was irradiated for 30 min in a microwave oven. Then the reaction solution was cooled to room temperature and concentrated at reduced pressure. The residue was purified by prep-HPLC to give desired library compounds as a solid.

$$\xrightarrow[\text{i-PrOH/H}_2\text{O, 120° C., 30 min, MW}]{\text{RBr or RI, Pd(dppf)Cl}_2,\ \text{Cs}_2\text{CO}_3}$$

6

Compounds 104, 105, 106, 108, 113, 119, 203 were prepared using this general procedure.

General procedure: A solution of 5 (200 mg, 0.35 mmol), R-305, R-306, or R308 (3.0 eq.), Pd$_2$(dba)$_3$ (25 mg, 0.03 mmol), t-BuOK (157 mg, 1.40 mmol), BINAP (22 mg, 0.03 mmol) in 5 mL of NMP was irradiated for 90 min at 150° C. in a microwave oven. Then the reaction solution was cooled to room temperature and concentrated at reduced pressure.

The residue was purified by prep-HPLC to desired compounds as a solid.

Compounds 305, 306, 308 were prepared using this general procedure.

General Procedures: To a solution of 5 (200 mg, 0.35 mmol), $K_3PO_4$ (149 mg, 0.70 mmol), DMCDA (7 mg, 0.05 mmol) and CuI (10 mg, 0.05 mmol) in 2 mL of DMF was added R-303 or R-304 (2.0 e.q). The resulting mixture was stirred at 120° C. overnight. The reaction mixture was cooled to room temperature, and water (0.5 mL) was added and extracted with EA (3 mL*3). The combined organic layers were dried over $Na_2SO_4$ and concentrated in vacuo. And the residue was purified by prep-HPLC to afford desired library compounds as a solid.

-continued

Compounds 303 and 304 were prepared using this general procedure.

Synthesis of Compound 107

$$DMF\text{---}DMA, 100°\,C., 2\,h$$
$$NH_2NH_2, EtOH, reflux, o/n$$

7

107

A solution of 7 (150 mg, 0.28 mmol) in DMF-DMA (3 mL) was stirred at 100° C. for 2 hours. Then the solution was cooled to room temperature and the solvent removed at reduced pressure. The crude residue was dissolved in EtOH (10 mL), and hydrazine (45 mg, 1.40 mmol) was added. The resulting mixture was heated to reflux overnight. The solvent was cooled to room temperature and concentrated in vacuo. The residue was purified by prep-HPLC to afford 107 (20 mg, 13%) as a solid.

Synthesis of Compound 207

Pd(PPh₃)₄, TEA, dioxane, 100° C., o/n

7 solvent free, 100° C., 5 h 7-1

NH₂OH, HCl, K₂CO₃

EtOH, reflux, 48 h

-continued

207

A solution of 7 (200 mg, 0.37 mmol) in DMA-DMA (4 mL) was heated to 100° C. and stirred for 2 hours. The excess DMA-DMA was evaporated in vacuo, and the residue was dissolved in ethanol (10 mL), to this solution was added K₂CO₃ (255 mg, 1.85 mmol) and hydroxylamine hydrochloride (77 mg, 1.11 mmol). The resulting mixture was refluxed overnight. After cooling, the mixture was filtered through celite and the filtrate was concentrated in vacuo. The residue was purified by prep-HPLC to afford compound 207 (18 mg, 8%) as a solid.

Synthesis of Compounds 870, 880, 8300, 831, 832

-continued

8300

870

831

880

832

Methods

8a R = Boc
8b R = Me

8b R = Me 8300, 831, 832

8a R = Boc 870, 880

63

1-(2-Methyl-5-nitrophenyl)guanidine (1)

A mixture of 2-methyl-5-nitroaniline (152 g, 1.0 mol), cyanamide (247 mL, 6.0 mol) and isopropyl alcohol (1000 mL) were placed in a 3 L flask. The mixture was heated to 80° C. Concentrated hydrochloric acid (57 mL) was slowly added dropwise over 80 min. The reaction mixture was stirred for 1 h while maintaining the temperature at 80° C. Another portion of concentrated hydrochloric acid (144 mL) was added dropwise at 80° C. The reaction mixture was then stirred for 12 h at 100° C. The mixture was cooled to room temperature and treated with aqueous NaOH (2.5 N, 1200 mL). The resulting solid was collected by filtration, washed with isopropyl alcohol (500 mL) and dried to afford compound 1 (145 g, 76% yield).

(E)-1-(5-Bromopyridin-3-yl)-3-(dimethylamino) prop-2-en-1-one (3)

A mixture of 3-acetyl-5-bromopyridine (126.7 g, 0.633 mol) and DMF-DMA (84 g, 70.6 mmol) was heated under reflux for 1 h. The mixture was cooled to room temperature and then directly purified by silica gel column chromatography. The resulting crude product after concentration was washed with diethyl ether (200 mL) and dried to afford compound 3 (122 g, 75.5% yield) as yellow crystals.

4-(5-Bromopyridin-3-yl)-N-(2-methyl-5-nitrophenyl)pyrimidin-2-amine (4)

A mixture of compound 1 (10.0 g, 51.5 mmol) and compound 3 (12.9 g, 50.8 mmol) in 2-propanol (150 mL) was heated under reflux for 18 h. The mixture was cooled to room temperature and the resulting precipitate was collected by filtration, washed with diethyl ether (100 mL) and dried to afford compound 4 (13.2 g, 67% yield) as pale yellow crystals.

N$^1$-(4-(5-Bromopyridin-3-yl)pyrimidin-2-yl)-6-methylbenzene-1,3-diamine (5)

A mixture of iron (5.0 8 g, 907 mmol), NH$_4$Cl (970 mg, 18.1 mmol) and SiO$_2$ (3 g) in ethanol/water (1:1, 140 mL) was heated at 55° C. for 10 min. Then a suspension of compound 4 (7.0 g, 18.1 mmol) in THF (70 mL) was added. The reaction mixture was stirred under reflux for 1 h and cooled to room temperature. The mixture was poured into water (100 mL) and then extracted with ethyl acetate (100 mL×2). The combined organic layers were washed with brine and water, dried over anhydrous sodium sulfate and concentrated to afford compound 5 (5.88 g, 91% yield) as yellow solid.

tert-Butyl 4-(4-(methoxycarbonyl)benzyl)piperazine-1-carboxylate (6a)

TFA (10 mL) was added dropwise to a mixture of methyl 4-formylbenzoate (20 g, 121 mmol) and tert-butyl piperazine-1-carboxylate (25 g, 134 mmol) in acetonitrile (400 mL) at room temperature. The mixture was stirred for 1 h and NaBH$_3$CN (8.32 g, 134 mmol) was added. The reaction mixture was stirred overnight at room temperature and water was added. The resulting mixture was extracted with ethyl acetate (100 mL×2). The combined organic layers were washed with brine and water, dried over anhydrous sodium sulfate and concentrated to afford compound 6a (14 g, 34.4% yield), which was used directly in the next step without further purification.

Methyl 4-(piperazin-1-ylmethyl)benzoate (6b)

Compound 6b was prepared from 1-methylpiperazine following the same procedure for 6a.

4-((4-(tert-Butoxycarbonyl)piperazin-1-yl)methyl) benzoic acid (7a)

A mixture of compound 6a (7.0 g, crude, 21 mmol) and LiOH—H$_2$O (1.4 g, 31 mmol) in methanol/acetonitrile/water (100 mL, 1:2:2) was stirred 1 h at room temperature. The organic solvent was removed and the remaining aqueous solution was washed with ethyl acetate (100 mL) and then adjusted to pH=2-3 with 2N aqueous HCl. The resulting mixture was extracted with ethyl acetate (30 mL×2). The combined extracts were dried over anhydrous sodium sulfate and concentrated to afford compound 7a (3.0 g, 44.8% yield) as a white solid.

4-(Piperazin-1-ylmethyl)benzoicacid (7b)

Compound 7b was prepared from 6b following the same procedure for 7a tert-Butyl 4-(4-(3-(4-(5-Bromopyridin-3-yl)pyrimidin-2-ylamino)-4-methyl phenylcarbamoyl)benzyl) piperazine-1-carboxylate (8a)

A mixture of compound 5 (1.0 g, 2.81 mmol), compound 7a (0.98 g, 4.19 mmol), HATU (1.28 g, 3.37 mmol) in DMF (20 mL) was cooled to 0° C. and DIPEA (1.95 mL, 11.24 mmol) was added. The reaction mixture was allowed to warm to room temperature and stirred for 15 min. Saturated aqueous sodium bicarbonate (20 mL) was added and the resulting mixture was extracted with ethyl acetate (50 mL×2). The combined extracts were dried over anhydrous sodium sulfate and concentrated. The residue was purified by flash column chromatography on silica gel (petroleum ether/ethyl acetate=3:1 to 1:1) to afford compound 8a (1.29 g, 80% yield) as a yellow solid.

N-(3-(4-(5-Bromopyridin-3-yl)pyrimidin-2-ylamino)-4-methylphenyl)-4-(piperazin-1-ylmethyl) benzamide (8b)

Compound 8b was prepared from 7b following the same procedure for 8a.

General Procedure for the Final Compounds 8300, 831, 832: A mixture of compound 8a/b (1.0 eq), the corresponding boronic acid (1.0 eq), Pd(dppf)Cl$_2$ (cat.) and Na$_2$CO$_3$ (2.5 eq) in 1-4-dioxane and water (5:1) was stirred at 80° C. for 1 h under N$_2$. The mixture was cooled to room temperature and then diluted with ethyl acetate and water. The resulting mixture was filtered and the filtrate was separated. The aqueous phase was extracted with ethyl acetate. The combined organic phases were washed with brine, dried over anhydrous sodium sulfate and concentrated to dryness. The residue was purified by flash column chromatography on silica gel or prep-HPLC to afford compound of interest as a yellow solid.

870: To a mixture of compound 8a (100 mg, 0.152 mmol), pyridin-4-ylboronic acid (21 mg, 0.167 mmol), Pd(dppf)Cl$_2$ (15 mg, cat.) and Na$_2$CO$_3$ (40 mg, 0.608 mmol) in 1-4- dioxane (2.5 mL) and water (0.5 mL) was stirred at 80° C. for 1 h under $N_2$. The mixture was cooled to room temperature and then diluted with ethyl acetate (10 mL) and water (10 mL). The resulting mixture was filtered and the filtrate was separated. The aqueous phase was extracted with EtOAc (20 mL×2). The combined organic phases were washed with brine (20 mL×2), dried over anhydrous and concentrated to dryness. The residue was purified by flash column chromatography on silica gel (DCM/MeOH=100:1 to 20:1) to afford compound Boc-870 (100 mg) as a brown solid.

TFA (1 mL) was added to a solution of Boc-870 (100 mg, 0.152 mmol) in $CH_2Cl_2$ (4 mL) at 0° C. with stirring. The reaction mixture was stirred for 1 h and concentrated to dryness. The residue was treated with aqueous $NaHCO_3$ to adjust pH=9 and then extracted with ethyl acetate (5 mL×3). The combined organic layers were washed with water and brine, dried over anhydrous sodium sulfate and concentrated. The residue was purified by flash column chromatography on silica gel (DCM/MeOH=20:1 to 10:1) to afford compound 870 (66 mg, 78.4% yield) as an off-white solid.

880: Compound 880 was prepared from pyridin-2-ylboronic acid following the same procedure for 870.

Synthesis of 810, 820, 830, 840, 8150, 8170, 8190, 8200, 8220, 8250, 8260, 8270, 8280, 8290

810

820

-continued

830

840

8150

8170

67

68

8190

8260

8200

8270

8220

8280

8250

8290

Methods

General Procedure for Compound 9 from Compound 4

810, 820, 830, 840

To a mixture of compound 4 (1.0 eq), the corresponding boronic acid (1.0 eq), Pd(dppf)Cl$_2$ (cat.) and Na$_2$CO$_3$ (2.5 eq) in 1-4-dioxane and water (5:1) was stirred at 80° C. for 1 h under N$_2$. The mixture was cooled to room temperature and then diluted with ethyl acetate and water. The resulting mixture was filtered and the filtrate was separated. The aqueous phase was extracted with ethyl acetate. The combined organic phases were washed with brine, dried over anhydrous sodium sulfate and concentrated to afford compound 9, which was used in the next step without further purification.

N-(2-Methyl-5-nitrophenyl)-4-(5-(4,4,5,5-tetramethyl-1,3,2-dioxaborolan-2-yl)pyridin-3-yl)pyrimidin-2-amine (11)

A mixture of compound 4 (5.0 g, 12.95 mmol), bis(pinacolato)diboron (3.62 g, 14.25 mmol), Pd(dppf)Cl$_2$ (0.3 g, cat.) and KOAc (3.83 g, 38.87 mmol) in toluene (50 mL) was heated under reflux for 12 h under N$_2$. The mixture was cooled to room temperature and diluted with ethyl acetate (100 mL) and water (100 mL). The resulting mixture was filtered and the filtrate was separated. The aqueous phase was extracted with ethyl acetate (100 mL×2). The combined organic phases were washed with brine (30 mL), dried over anhydrous sodium sulfate and concentrated to dryness. The residue was purified by flash column chromatography on silica gel (Petroleum/EtOAc=20:1) to afford compound 11 (4.77 g, 84.3% yield) as a brown solid.

General Procedure for Compound 9 from Compound 11

8150, 8170, 8190, 8200, 8220, 8250, 8260, 8270, 8280, 8290

A mixture of Ar-X (1.0 eq), compound 11 (1.1 eq), Pd(dppf)Cl$_2$ (cat.) and Na$_2$CO$_3$ (3.0 eq) in 1-4-dioxane and water (5:1) was stirred at 80° C. for 1 h under N$_2$. The mixture was cooled to room temperature and diluted with ethyl acetate and water. The resulting mixture was filtered and the filtrate was separated. The aqueous phase was extracted with ethyl acetate and the combined organic phases were washed with brine, dried over anhydrous sodium sulfate and concentrated to afford compound 9, which was used in the next step without further purification.

General Procedure for Compound 10

A mixture of iron (5.0 eq), NH$_4$Cl (1.0 eq) and SiO$_2$ (2.0 eq) in ethanol/water (1:1) was heated at 55° C. for 10 min. Then a suspension of compound 9 (1.0 eq) in THF was added. The reaction mixture was stirred under reflux for 1 h and cooled to room temperature. The mixture was poured into water and then extracted with ethyl acetate. The combined organic layers were washed with brine and water, dried over anhydrous sodium sulfate and concentrated to afford compound 10 as a yellow solid.

General Procedure for the Final Compound

A mixture of compound 10 (1.0 eq), compound 7b (1.2 eq) and HATU (1.2 eq) in DMF (20 mL) was cooled to 0° C. and DIPEA (4.0 eq) was added. The reaction mixture was allowed to warm to room temperature and stirred for 15 min. Saturated aqueous sodium bicarbonate was added and the resulting mixture was extracted with ethyl acetate. The combined extracts were dried over anhydrous sodium sulfate and concentrated. The residue was purified by flash column chromatography on silica gel to afford the desired compound as a solid.

Synthesis of 806, 809, 8120, 8130, 8180, 8230, 8140

806

809

8120

8130

8180

8230

8240

-continued

12

13

14

X-Int

15

16

809, 8120, 8130
8180, 8230, 8240
806
R = Me
R = H

7a R = Boc
7b R = Me
HATU

4-Methoxy-N-(2-methyl-5-nitrophenyl)pyrimidin-2-amine (12)

To a mixture of 2-chloro-4-methoxypyrimidine (9.54 g, 66 mmol), 2-methyl-5-nitrobenzenamine (10.0 g, 66 mmol), $Pd_2(dba)_3$ (1.0 g), S-Phos (1.0 g, 24.4 mmol), and $Cs_2CO_3$ (31.8 g, 99 mmol) in 1,4-dioxane/water (140 mL/60 mL) was heated at 110° C. overnight. The mixture was cooled to room temperature and then filtered through a pad of celite. The filtrate was diluted with ethyl acetate and washed with water. The organic phase was dried over anhydrous sodium sulfate and concentrated. The residue was purified by flash column chromatography on silica gel to afford compound 12 (12 g.70.6% yield) as a light yellow solid.

2-(2-Methyl-5-nitrophenylamino)pyrimidin-4-ol (13)

A mixture of compound 12 (20 g, 77 mol), TMSCl (15 g, 136 mmol) and NaI (23.4 g, 156 mmol) in acetonitrile (400 mL) was heated at 120° C. overnight. The mixture was cooled to room temperature and 2N aqueous $Na_2CO_3$ (400 mL) and DCM (400 mL) were added. The organic layer was separated, washed with water, dried over anhydrous sodium sulfate and concentrated. The residue was purified by flash column chromatography on silica gel (DCM/MeOH=200:1) to afford compound 13 (12.1 g, 64% yield) as a light yellow solid.

4-Chloro-N-(2-methyl-5-nitrophenyl)pyrimidin-2-amine (14)

A mixture of compound 13 (2 g, 8.13 mmol) and DMF (5 drops) in POCl$_3$ (40 mL) was heated under reflux for 2 h. The mixture was cooled to room temperature and most of POCl$_3$ was removed. The residue was poured into aqueous NaOH (100 mL) carefully and the resulting mixture was extracted with DCM (100 mL×2). The combined organic layers were washed with brine and water (100 mL), dried over anhydrous sodium sulfate and concentrated to afford compound 14 (2.0 g, 93% yield) as a yellow solid.

General Procedure for Compound 15

A mixture of compound 14 (1.0 eq), X-Int (1.0 eq), Pd(dppf)Cl$_2$ (cat.) and K$_2$CO$_3$ (3.0 eq) in 1-4-dioxane (20 mL) and water (20 mL) was heated under reflux for 12 h under N$_2$. The mixture was cooled to room temperature and diluted with ethyl acetate and water. The resulting mixture was filtered and the filtrate was separated. The aqueous phase was extracted with ethyl acetate. The combined organic phases were washed with brine, dried over anhydrous sodium sulfate and concentrated to dryness. The residue was purified by flash column chromatography on silica gel (DCM/MeOH=200:1) to afford compound 15 as a yellow solid.

General Procedure for Compound 16

To a mixture of iron (1.0 eq), NH$_4$Cl (2.0 eq) and SiO$_2$ (cat) in ethanol/water (1:1) was heated at 55° C. for 10 min. Then a suspension of compound 15 (2.0 eq) in THF was added. The reaction mixture was stirred under reflux for 1 h and cooled to room temperature. The mixture was poured into water and then extracted with ethyl acetate. The combined organic layers were washed with brine and water, dried over anhydrous sodium sulfate and concentrated to afford compound 16.

Procedure for 806

A mixture of compound 16 (Het=3-methylisoxazol-5-yl, 150 mg, 0.42 mmol), compound 7a (134 mg, 0.42 mmol) and HATU (159 mg, 0.42 mmol) in DMF (2 mL) was cooled to 0° C. and DIPEA (217 mg, 1.68 mmol) was added. The reaction mixture was allowed to warm to room temperature and stirred for 15 min. Saturated aqueous sodium bicarbonate was added and the resulting mixture was extracted with ethyl acetate. The combined extracts were dried over anhydrous sodium sulfate and concentrated. The residue was purified by flash column chromatography on silica gel (Petroleum ether/ethyl acetate=1:1 to ethyl acetate) to afford compound Boc-806 (180 mg, 65.2% yield) as a solid.

HCl/EtOAc (2N, 1 mL) was added to a solution of Boc-806 (97 mg, 0.147 mmol) in EtOAc (1 mL) at 0° C. with stirring. The reaction mixture was stirred for 1 h and the resulting precipitate was collected by filtration, washed with DCM and dried to afford compound 806 (HCl salt, 80 mg, 100% yield) as a yellow solid.

General Procedure 806, 809, 8120, 8130, 8180, 8230 and 8240

A mixture of compound 16 (1.0 eq), compound 7b (1.0 eq) and HATU (1.0 eq) in DMF (2 mL) was cooled to 0° C. and DIPEA (4.0 eq) was added. The reaction mixture was allowed to warm to room temperature and stirred for 15 min. Saturated aqueous sodium bicarbonate was added and the resulting mixture was extracted with ethyl acetate. The combined extracts were dried over anhydrous sodium sulfate and concentrated. The residue was purified by flash column chromatography on silica gel (DCM/MeOH=20:1) to afford final compound as a yellow solid.

Example 2: Inhibition of Abelson Protein Kinases c-Abl1, c-Abl2 and c-Kit and Comparison to Imatinib, the Active Ingredient in Gleevec®

| Cpd | c-Abl1 (nM) | c-Abl2 (nM) | c-Kit (nM) |
|---|---|---|---|
| 101 | 232.35 | 224.57 | 6.80 |
| 102 | 95.33 | 169.62 | 6.70 |
| 103 | 200.41 | 212.18 | 7.70 |
| 107 | 45.17 | 66.95 | 7.20 |
| 108 | 40.53 | 85.88 | 7.40 |
| 113 | 35.00 | 50.11 | 7.50 |
| 114 | 101.53 | 142.60 | 32.40 |
| 115 | 107.81 | 202.79 | 8.90 |
| 116 | 91.06 | 160.89 | 11.60 |
| 117 | 29.13 | 34.99 | 5.70 |
| 118 | 37.16 | 51.00 | 8.40 |
| 119 | 117.66 | 44.68 | 4.00 |
| 201 | 193.18 | 514.16 | 19.30 |
| 202 | 403.88 | 701.00 | 31.10 |
| 203 | 250.56 | 711.96 | 47.10 |
| 207 | 30.19 | 73.73 | 12.20 |
| 303 | 162.15 | 349.36 | 18.90 |
| 305 | 397.83 | 631.35 | 9.20 |
| 309 | 174.37 | 149.18 | 14.00 |
| 401 | 167.28 | 178.63 | 12.40 |
| 402 | 183.14 | 207.42 | 11.10 |
| 404 | 100.32 | 116.17 | 5.80 |
| 405 | 107.09 | 150.43 | 5.90 |
| 806 | 84 | 152 | 13 |
| 809 | 47 | 77 | 7.8 |
| 820 | 84 | 173 | 10 |
| 830 | 34 | 51 | 6.0 |
| 832 | 53 | 77 | 4.0 |
| 880 | 203 | 341 | 12 |
| 8120 | 476 | 783 | 27 |
| 8130 | 323 | 423 | 44 |
| 8170 | 128 | 182 | 11 |
| 8180 | 369 | 303 | 13 |
| 8190 | 97 | 91 | 9.7 |
| 8200 | 96 | 131 | 4.3 |
| 8230 | >1000 | >1000 | 37 |
| 8240 | >1000 | >1000 | 39 |
| 8250 | 71 | 216 | 15 |
| 8260 | 41 | 236 | 16 |
| 8270 | 53 | 100 | 4.9 |
| 8280 | 57 | 104 | 6.2 |
| 8290 | 51 | 137 | 5.7 |
| 8300 | 40 | 39 | 5.2 |
| imatinib | 828.3 | 1000 | 30.7 |

Kinase base buffer (50 mM HEPES, pH 7.5 0.0015% Brij-35; 10 mM MgCl$_2$ 2 mM DTT) and Stop buffer (100 mM HEPES, pH 7.5 0.015% Brij-35; 0.2% Coating Reagent (50 mM EDTA) are prepared. Test compound is diluted in 100% DMSO to 50-times the desired final inhibitor concentration (the Stock Solution) and serially diluted in half-log increments resulting in final concentrations 250 μM to 75 μM, 25 μM, 7.5 μM, 2.5 μM, 0.75 μM, 0.25 μM, 75 nM, 25 nM, 7.5 nM in DMSO. 10 μl of each compound is placed in a 96-well plate as the intermediate plate. 90 μl of Kinase Buffer is added to to each well to prepare the intermediate plate. Mix the compounds in intermediate plate for 10 min on shaker. For the assay of enzyme inhibitions, 5 μl of each well from the intermediate plate is transferred to a 384-well plate in duplicates, 10. Then 10 μl of 2.5× enzyme solution is added to each well of the 384-well assay plate and incubated for 10 min. Then enzyme substrate is added as 10 μl of 2.5×FAM-labeled peptide+ATP solution to each well of the 384-well assay plate The reaction is allowed to proceed at 28° C. and quenched with the addition of 25 μl of stop buffer. The release of fluorescent FAM is quantitated as Percent inhibition=(max−conversion)/(max−min)*100. "max" stands for DMSO control; "min" stands for low control. Data are fit in XLFit excel add-in version 4.3.1 to obtain IC50 values. Equation used is: Y=Bottom+(Top–Bottom)/(1+(IC50/X)^HillSlope).

Example 3: Inhibition Profile of a 500 nM Solution of Test Compounds Against 14 Protein Kinases Kinase base buffer (50 mM HEPES, pH 7.5 0.0015% Brij-35; 10 mM MgCl₂ 2 mM DTT) and Stop buffer (100 mM HEPES, pH 7.5 0.015% Brij-35; 0.2% Coating Reagent (50 mM EDTA) are prepared. Test compound is diluted in 100% DMSO to 50-times the desired final inhibitor concentration (the Stock Solution) in DMSO. 10 µl of each compound is placed in a 96-well plate as the intermediate plate. 90 µl of Kinase Buffer is added to to each well to prepare the intermediate plate. Mix the compounds in intermediate plate for 10 min on shaker. For the assay of enzyme inhibitions, 5 µl of each well from the intermediate plate is transferred to a 384-well plate in duplicates, 10. Then 10 µl of 2.5× enzyme solution is added to each well of the 384-well assay plate and incubated for 10 min. Then enzyme substrate is added as 10 µl of 2.5×FAM-labeled peptide+ATP solution to each well of the 384-well assay plate The reaction is allowed to proceed at 28° C. and quenched with the addition of 25 µl of stop buffer. The release of fluorescent FAM is quantitated as Percent inhibition=(max–conversion)/(max–min)*100.sp; "max" stands for DMSO control; "min" stands for low control. Convert conversion values to inhibition values. Percent inhibition=(max–conversion)/(max–min)*100. "max" stands for DMSO control; "min" stands for low control.

TABLE 1

| Cpd | YES | PDG FRa | LCK | SRC | ABL | FLT3 | KIT | PDG FRb | FGR | LYNA | ARG/ Abl2 | FES | FYN | JNK2 |
|---|---|---|---|---|---|---|---|---|---|---|---|---|---|---|
| 101 | 100 | 42 | 88 | 18 | 73 | 36 | 87 | 99 | 55 | 89 | 74 | 43 | 52 | 25 |
| 102 | 99 | 39 | 91 | 19 | 83 | 32 | 99 | 99 | 67 | 88 | 75 | 42 | 55 | 26 |
| 103 | 101 | 42 | 91 | 25 | 71 | 28 | 92 | 98 | 60 | 91 | 71 | 38 | 54 | 17 |
| 107 | 101 | 59 | 95 | 28 | 91 | 51 | 99 | 101 | 82 | 93 | 87 | 28 | 69 | 1.7 |
| 108 | 100 | 56 | 94 | 34 | 91 | 73 | 100 | 101 | 80 | 93 | 88 | 67 | 66 | 36 |
| 113 | 100 | 61 | 94 | 37 | 92 | 25 | 98 | 101 | 85 | 95 | 91 | 26 | 75 | 18 |
| 114 | 100 | 34 | 77 | 18 | 84 | 20 | 99 | 99 | 81 | 91 | 78 | 17 | 72 | 18 |
| 115 | 100 | 53 | 90 | 29 | 83 | 22 | 96 | 99 | 78 | 93 | 76 | 20 | 67 | 17 |
| 116 | 100 | 48 | 94 | 29 | 87 | 8.4 | 93 | 101 | 83 | 93 | 76 | 19 | 67 | 5.9 |
| 117 | 99 | 74 | 97 | 55 | 94 | 13 | 95 | 99 | 90 | 97 | 91 | 24 | 86 | 14 |
| 118 | 99 | 66 | 95 | 35 | 92 | 61 | 93 | 101 | 84 | 96 | 88 | 38 | 77 | 14 |
| 119 | 99 | 67 | 98 | 53 | 83 | 90 | 95 | 100 | 86 | 97 | 90 | 47 | 82 | 42 |
| 201 | 99 | 45 | 91 | 18 | 72 | 30 | 91 | 98 | 67 | 87 | 55 | 49 | 53 | 6.1 |
| 202 | 100 | 46 | 87 | 16 | 64 | 19 | 85 | 98 | 64 | 87 | 50 | 27 | 47 | 19 |
| 203 | 100 | 29 | 88 | 17 | 72 | 31 | 77 | 95 | 59 | 82 | 54 | 21 | 43 | 17 |
| 207 | 100 | 54 | 95 | 30 | 94 | 19 | 88 | 99 | 79 | 92 | 85 | 31 | 72 | 19 |
| 303 | 100 | 33 | 87 | 13 | 79 | 25 | 87 | 100 | 58 | 86 | 62 | 31 | 45 | 4.7 |
| 305 | 100 | 16 | 80 | 10 | 62 | 20 | 98 | 100 | 47 | 80 | 50 | 47 | 25 | 4.4 |
| 309 | 101 | 25 | 84 | 13 | 77 | 13 | 96 | 99 | 59 | 87 | 79 | 31 | 44 | 24 |
| 401 | 100 | 40 | 88 | 18 | 76 | 24 | 98 | 99 | 67 | 90 | 81 | 19 | 50 | 23 |
| 402 | 100 | 29 | 86 | 19 | 72 | 31 | 96 | 100 | 65 | 89 | 75 | 23 | 48 | 21 |
| 404 | 100 | 47 | 91 | 21 | 82 | 24 | 97 | 100 | 75 | 90 | 83 | 32 | 56 | 34 |
| 405 | 101 | 33 | 90 | 16 | 80 | 29 | 95 | 100 | 68 | 90 | 80 | 33 | 52 | 28 |

TABLE 2

| Cpd | Abl2 | Abl1 | PDGFRa | PDGFRb | JNK1 | JNK2 | SRC | LCK | CMT | FES | YES | FYN | LYNA | FLT3 | FGR |
|---|---|---|---|---|---|---|---|---|---|---|---|---|---|---|---|
| 810 | 59 | 65 | 99 | 98 | 25 | 48 | 20 | 83 | 85 | 23 | 44 | 71 | 93 | 26 | 57 |
| 820 | 76 | 85 | 99 | 98 | 12 | 29 | 23 | 88 | 87 | 32 | 56 | 73 | 91 | 61 | 64 |
| 830 | 87 | 92 | 100 | 99 | 23 | 52 | 38 | 93 | 92 | 22 | 63 | 81 | 97 | 44 | 77 |
| 831 | 60 | 48 | 100 | 97 | 15 | 17 | 12 | 82 | 82 | 23 | 25 | 57 | 87 | 38 | 34 |
| 832 | 81 | 88 | 100 | 100 | 24 | 16 | 28 | 93 | 91 | 24 | 66 | 79 | 106 | 58 | 80 |
| 840 | 30 | 38 | 99 | 92 | 24 | 56 | 15 | 50 | 73 | 35 | 25 | 64 | 77 | 69 | 24 |
| 870 | 60 | 60 | 100 | 97 | 17 | 37 | 17 | 70 | 82 | 39 | 23 | 58 | 83 | 73 | 38 |
| 880 | 61 | 71 | 100 | 100 | 28 | 48 | 15 | 70 | 87 | 35 | 33 | 64 | 80 | 62 | 46 |
| 8150 | 54 | 42 | 99 | 97 | 31 | 42 | 14 | 77 | 83 | 26 | 26 | 62 | 90 | 68 | 34 |
| 8170 | 73 | 78 | 100 | 98 | 32 | 40 | 25 | 88 | 86 | 67 | 49 | 70 | 93 | 79 | 68 |
| 8190 | 81 | 82 | 100 | 99 | 41 | 58 | 28 | 92 | 86 | 51 | 52 | 74 | 96 | 72 | 71 |
| 8200 | 75 | 78 | 98 | 97 | 41 | 54 | 22 | 92 | 85 | 52 | 50 | 65 | 100 | 68 | 63 |
| 8220 | 54 | 44 | 99 | 97 | 56 | 50 | 22 | 90 | 83 | 57 | 40 | 75 | 93 | 75 | 47 |
| 8250 | 68 | 87 | 100 | 98 | 15 | 8 | 20 | 87 | 80 | 37 | 45 | 74 | 85 | 68 | 63 |
| 8260 | 67 | 85 | 100 | 101 | 21 | 15 | 22 | 83 | 79 | 16 | 41 | 71 | 88 | 62 | 60 |
| 8270 | 80 | 91 | 99 | 98 | 41 | 36 | 33 | 91 | 88 | 60 | 60 | 83 | 104 | 78 | 81 |
| 8280 | 80 | 90 | 100 | 99 | 23 | 14 | 28 | 82 | 89 | 32 | 53 | 76 | 98 | 54 | 78 |
| 8290 | 75 | 86 | 100 | 100 | 33 | 23 | 26 | 87 | 88 | 36 | 55 | 76 | 98 | 63 | 75 |
| 8300 | 89 | 92 | 99 | 98 | 35 | 30 | 45 | 97 | 88 | 19 | 63 | 90 | 108 | 61 | 81 |

Example 4: Pharmacokinetic Parameters of Certain Compounds of the Invention

Various pharmacokinetic parameters of the compounds described herein were measured in Sprague-Dawley rats. The results of are presented in Table 3.

TABLE 3

| | Compound: | | | | | |
|---|---|---|---|---|---|---|
| | 207 | 832 | 809 | 8270 | 830 | imatinib |
| $C_{max}$ (ng/mL) | 225.3 ± 83.8 | 415.8 ± 84.5 | 170.5 | 210 ± 31 | 465 ± 115 | 241 |
| $t_{max}$ (h) | 5.3 ± 1.2 | 4.0 ± 0 | 4 | 5.3 | 4 | 4 |
| $t_{1/2}$ (h) | 3.1 ± ND | 2.6 ± 0 | 2.2 | 3.3 | 3.6 | ≈3 |
| $AUC_{last}$ (h*ng/mL) | 1647 ± 1084 | 3178.3 ± 930 | 1065 | 1760 ± 268 | 3715 ± 1090 | 2726 |
| CL (L/h/kg) | 2 ± 0.34 | 1.3 ± 0.74 | 2.7 | 2.6 ± 0.41 | 1.3 ± 0.33 | 0.57 |
| $V_d$ (L/kg) | 6.5 ± 0.96 | 3.6 ± 1.8 | 7.2 | 7.8 ± 0.70 | 6.3 ± 1.1 | 1.1 |
| Bioavailability | 32% ± 21% | 33% ± 10% | 24% | 46% ± 7% | 47% ± 14% | ≈53% |
| Caco-2 permeability ratio influx:efflux | 0.44 | 0.63 | 0.58 | 2.2 | 0.52 | 0.67 |
| Human liver microsome $t_{1/2}$ (min) | 17.51 | 24.46 | 21.86 | 20.87 | 19.56 | 34.82 |
| Serum protein binding | 85.9% | ND | 85.7% | ND | ND | >98% |
| Fold-improvement in brain penetration | 2.7 | 5.3 | 4.5 | 2.5 | ND | 1 |

Example 5: Mouse MPTP Neurotoxicity Model

Certain compounds of the present invention were evaluated using the MPTP neurotoxicity model. MPTP causes oxidative stress, which in turn causes c-Abl1 and/or c-Abl2 phosphorylation in the SNpc of mice treated with MPTP. MPTP administration according to this model produces a reliable, irreversible loss of DA neurons 7 days after the last injection, similar to that observed in PD. MPTP causes greater loss of DA neurons in SNpc and degeneration of DA nerve terminals in the caudate putamen. Many of the cell death signaling events observed in PD postmortem tissue are present in the MPTP model including oxidative stress, nitrosative stress, c-Abl activation, Parkin inactivation and PARIS and AIMP2 elevation and PARP activation. The ATK inhibitors imatinib and nilotinib provide neuroprotection in the acute MPTP-induced model of PD. Because the model is relatively rapid, this model was used to assess dosing for future studies, and as a preliminary measure of efficacy.

Figure 1:
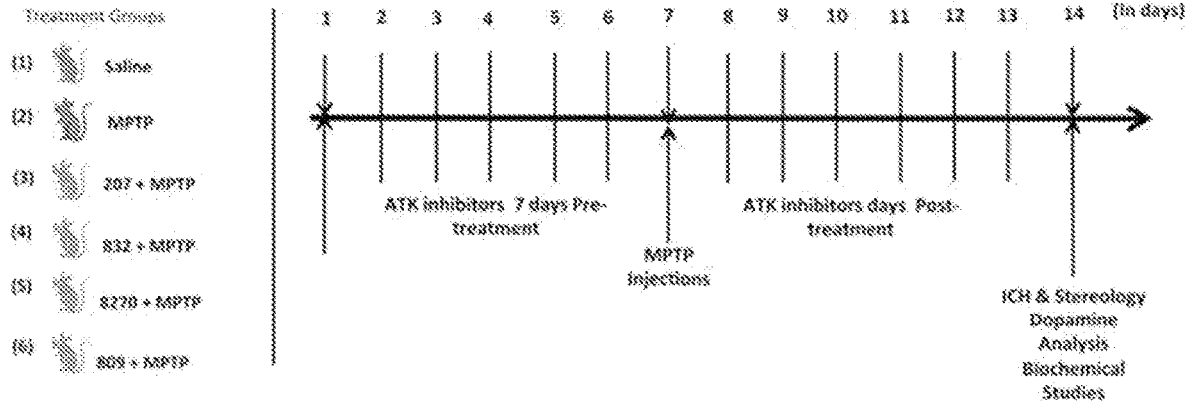
FIG. 1 shows the experimental design of a study investigating certain compounds of the invention in a mouse model for Parkinson's disease.

The study design is depicted in FIG. 1. Compounds 207, 832, 8270, and 809 were tested. Wild type mice (n=5 per group) were divided into 4 treatment groups as follows: saline, MPTP, Drug and MPTP+Drug. Saline and MPTP groups were pre-treated with drug vehicle (unbuffered water) (20 animals total). Drug and MPTP+Drug groups received the test compounds for 6 days administered by oral gavage daily. On the seventh day, the saline and Drug groups received four intra-peritoneal (i.p.) injections of saline at 2 h intervals. The MPTP and MPTP+Drug groups received four intraperitoneal (i.p.) injections of MPTP·HCl (20 mg/kg free base) at 2 hr intervals. After the MPTP injection day, mice were treated for an additional 6 days with saline or an ATK inhibitor of the present invention. Mice in the saline and MPTP only groups received saline vehicle while the Drug and MPTP+Drug groups received an additional week of drug treatment. On the 14th day, mice were given a pole test, then sacrificed. Brain samples were processed for analysis of biogenic amine concentrations, including dopamine (DA), by high-performance liquid chromatography with electrochemical detection (HPLC-ECD). Loss of DA and its metabolites in the striatum is a consistently reliable indication of loss of DA neurons in the SNpc.

Figure 2:
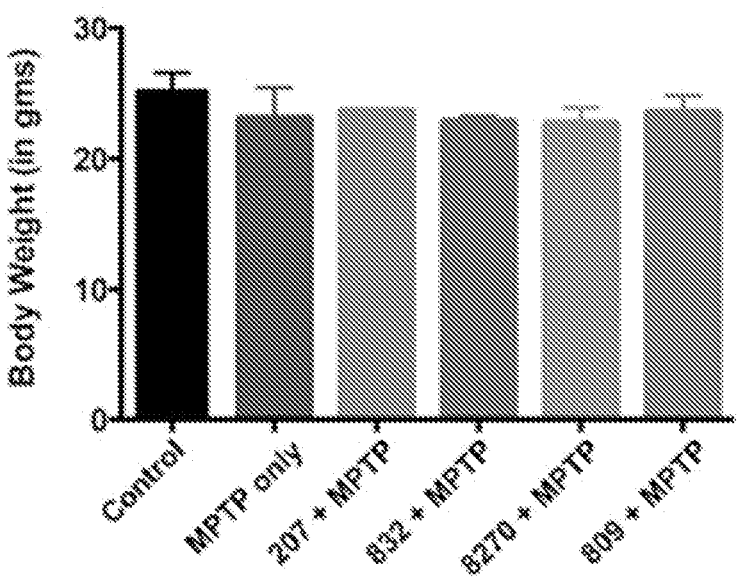
FIG. 2 shows the effects of certain compounds of the invention on body weight in the MPTP model for Parkinson's disease.
Figure 3:
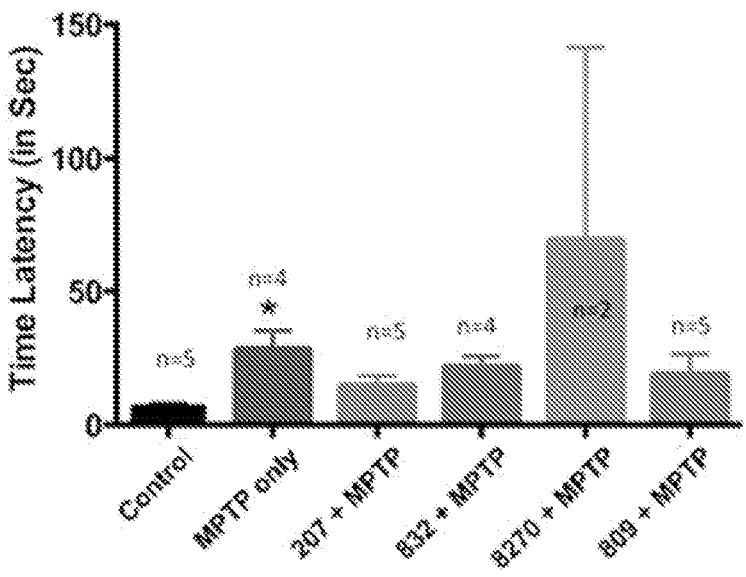
FIG. 3 shows the effects of certain compounds of the invention on pole test results in the MPTP model for Parkinson's disease.

None of the tested compounds caused significant body-weight loss (FIG. 2). In the pole test (FIG. 3), the control animals had a latency of about 5 seconds, while the MPTP animals tool about 30. Animals treated with 207, 832, and 809 recovered to a near-normal latency time. The result for 8270 was not statistically significant.

Figure 4:
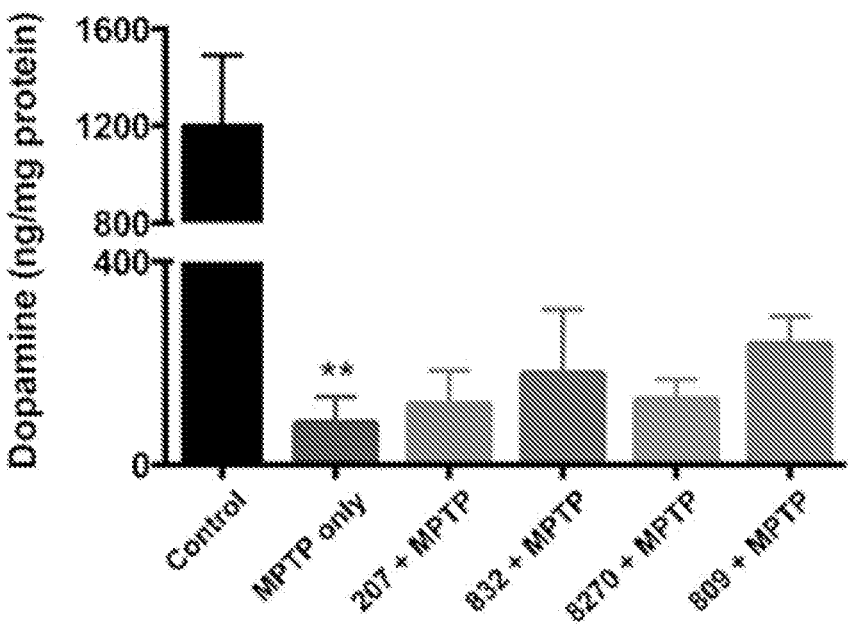
FIG. 4 shows the effects of certain compounds of the invention on dopamine levels in the MPTP model for Parkinson's disease.

Dopamine secretion measurements test whether dopamine-secreting cells are being protected from degradation by ATK inhibition. Compounds 207, 832, 8270, and 809 all protected dopamine-secreting neurons from degeneration, although not equally (FIG. 4).

Figure 5:
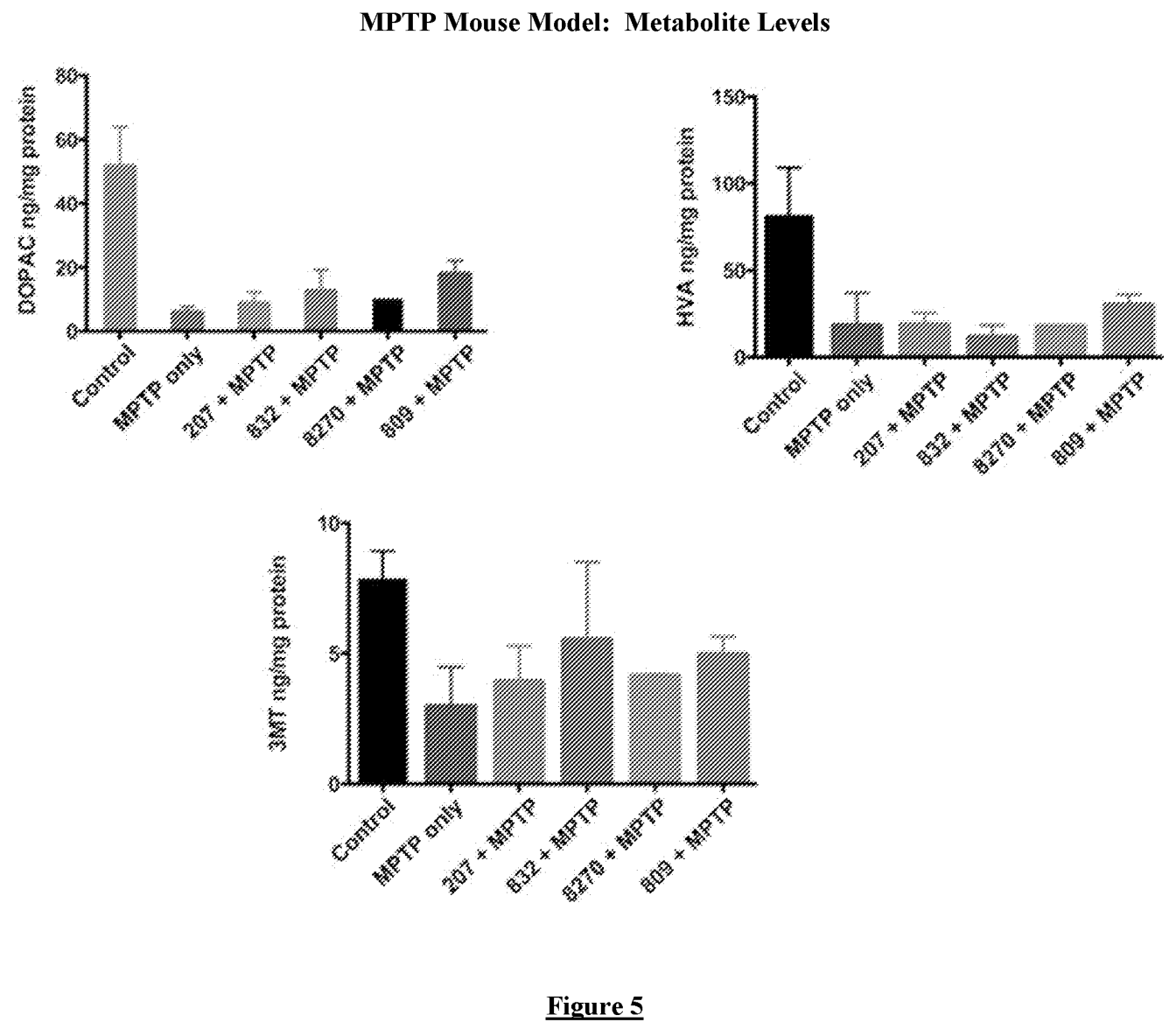
Figure 6:
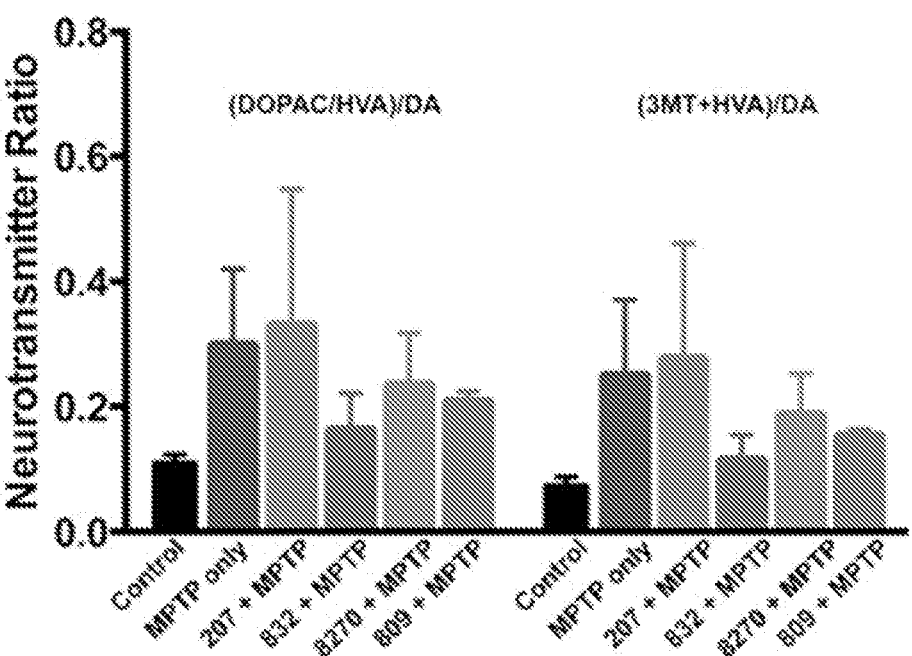
FIG. 6 shows the effects of certain compounds of the invention on dopamine turnover ratios in the MPTP model for Parkinson's disease.

The levels of metabolites of dopamine in the test animals were measured. All four tested compounds protected loss of 3,4-Dihydroxyphenylacetic acid (DOPAC) and 3-methoxy-tyramine (3MT) to differing extents (FIG. 5). The dopamine turnover ratio was also measured. Some of the tested compounds recovered the turnover ratio observed in the control animals, others did not show a statistically significant result (FIG. 6)

The phosphorylation level of c-Abl in the ventral midbrain was measured in the group that received Compound 809. Compound 809 provided full recovery of the c-Abl phosphorylation levels observed in the control group (FIG. 7 (left).)

Example 6: Functional Rescue Study in Mutated Alpha-Synuclein Model

Functional rescue by exemplary compounds of the present disclosure is demonstrated using a mutated alpha-synuclein model of Parkinson's Disease. The A53T mutant of alpha-synuclein is a clinically identified mutation that leads to hyper aggregation of alpha-synuclein in mice, and recapitulates the symptoms of Parkinson's disease such as dopaminergic neuron loss.

A53T synuclein mice are treated with a compound of the present disclosure (for example compound 809). Mice so treated fail to display the characteristics of dopaminergic neuron loss. This effect is believed to be due to the compound blocking formation of the toxic form of A53T-alpha-synuclein by inhibiting c-Abl.

Example 7: Functional Rescue Study in Alpha-Synuclein Fibril Model

Injection of pre-formed alpha-synuclein fibrils is known to induce Parkinson's-like disease in mice. Mice that have been injected with pre-formed alpha-synuclein fibrils are treated with a compound of the present disclosure (for example compound 809). Mice so treated fail to exhibit Parkinson's like disease because. This effect is believes to be due to the compound blocking the formation of toxic pre-formed-fibril alpha synuclein by inhibiting c-Abl.

INCORPORATION BY REFERENCE

Each of the patents, published patent applications, and non-patent references cited herein are hereby incorporated by reference in their entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of treating Parkinson's disease comprising administering to a subject an effective amount of an ATK inhibitor, wherein the ATK inhibitor is a compound having a structure of Formula (I), or a pharmaceutically acceptable salt thereof:

Formula (I)

wherein, independently for each occurrence, $R^1$ is hydrogen, lower alkyl, —$CH_3$, —$CDH_2$, —$CD_2H$, or —$CD_3$; and $Cy^1$ is substituted or unsubstituted, 5-membered heteroaryl.

2. The method of claim 1, wherein Cy1 is selected from:

and wherein, independently for each occurrence, $R^2$ and $R^3$ are each independently selected from hydrogen, alkyl, amino, monoalkylamino, dialkylamino, cycloalkyl, halo, cyano, alkoxy, —C(O)OH, and —$C(O)N(R^4)$ ($R^4$); and each $R^4$ is independently selected from hydrogen and substituted or unsubstituted alkyl, aralkyl, cycloalkyl, heterocyclyl, aryl, heteroaryl, heteroaralkyl, cycloalkylalkyl, or heterocyclylalkyl.

3. The method of claim 1, wherein $Cy^1$ is selected from:

and

4. The method of claim 1, wherein the compound is of the formula:

or a pharmaceutically acceptable salt thereof.

5. The method of claim 4, wherein the compound is a methanesulfonic acid salt.

6. The method of claim 4, wherein the compound is a succinic acid salt.

7. The method of claim 4, wherein the compound is a free base.

8. The method of claim 1, wherein the ATK inhibitor is administered orally or parenterally.

9. The method of claim 4, wherein the ATK inhibitor is administered orally or parenterally.

10. The method of claim 5, wherein the ATK inhibitor is administered orally or parenterally.

11. The method of claim 6, wherein the ATK inhibitor is administered orally or parenterally.

12. The method of claim 7, wherein the ATK inhibitor is administered orally or parenterally.

13. The method of claim 1, wherein $Cy^1$ is of the formula:

wherein, independently for each occurrence, $R^1$ is hydrogen or lower alkyl;

$R^2$ and $R^3$ are each independently hydrogen, alkyl, amino, monoalkylamino, dialkylamino, cycloalkyl, halo, cyano, alkoxy, —C(O)OH, or —C(O)N($R^4$)($R^4$); and each $R^4$ is independently selected from hydrogen and substituted or unsubstituted alkyl, aralkyl, cycloalkyl, heterocyclyl, aryl, heteroaryl, heteroaralkyl, cycloalkylalkyl, and heterocyclylalkyl.

14. The method of claim 1, wherein $Cy^1$ is of the formula:

15. The method of claim 1, wherein $Cy^1$ is of the formula:

16. The method of claim 2, wherein $Cy^1$ is of the formula:

17. The method of claim 1, wherein $Cy^1$ is of the formula:

18. The method of claim 1, wherein $R^1$ is —$CH_3$, —$CDH_2$, —$CD_2H$, or —$CD_3$.

19. The method of claim 1, wherein the compound is of the formula:

| Formula | R |
| --- | --- |
| | |
| | |
| | |

-continued

| Formula | R |
|---------|---|
| | |
| | |
| | |
| | |

-continued

| Formula | R |
|---|---|

-continued

| Formula | R |
|---|---|

-continued

| Formula | R |
| --- | --- |

-continued

| Formula | R |
|---------|---|

-continued

| Formula | R |
|---|---|

-continued

| Formula | R |
|---------|---|

-continued

| Formula | R |
| --- | --- | or a pharmaceutically acceptable salt thereof.

20. The method of claim 1, wherein the compound is a quaternary ammonium salt.

21. The method of claim 4, wherein the compound is a quaternary ammonium salt.

22. The method of claim 19, wherein the compound is a quaternary ammonium salt.

\* \* \* \* \*